United States Patent [19]

Middleton

[11] 4,393,074

[45] Jul. 12, 1983

[54] FLUORINATED CARBAMATE INSECTICIDES

[75] Inventor: William J. Middleton, Chadds Ford, Pa.

[73] Assignee: E. I. Du Pont de Nemours and Company, Wilmington, Del.

[21] Appl. No.: 338,476

[22] Filed: Jan. 11, 1982

Related U.S. Application Data

[60] Division of Ser. No. 139,797, Apr. 14, 1980, Pat. No. 4,323,578, which is a continuation-in-part of Ser. No. 65,485, Sep. 10, 1979, abandoned.

[51] Int. Cl.$^3$ .................. A01N 43/08; C07C 119/18; A01N 37/52
[52] U.S. Cl. .................. 424/285; 260/453.3; 549/470; 424/298
[58] Field of Search .................. 260/453.3; 549/470; 424/298, 285

[56] References Cited

U.S. PATENT DOCUMENTS

| | | | |
|---|---|---|---|
| 3,576,834 | 4/1971 | Buchanan | 260/453 |
| 4,004,031 | 1/1977 | Drabek | 260/453 |
| 4,117,154 | 9/1978 | Stettar et al. | 424/298 |

FOREIGN PATENT DOCUMENTS

| | | | |
|---|---|---|---|
| 848911 | 5/1977 | Belgium | 260/453 |
| 848912 | 5/1977 | Belgium | 260/453 |
| 848913 | 5/1977 | Belgium | 260/453 |

*Primary Examiner*—Henry R. Jiles
*Assistant Examiner*—Robert C. Whittenbaugh

[57] ABSTRACT

Fluorinated carbamoyl sulfides, such as N,N'[thiobis[-(methylimino)carbonyloxy]]bis[2,2,2-trifluoroethanimidothioic acid], dimethyl ester, useful for control of insects.

9 Claims, No Drawings

FLUORINATED CARBAMATE INSECTICIDES

CROSS-REFERENCE TO RELATED APPLICATIONS

This application is a divisional of Patent Application Ser. No. 139,797 now U.S. Pat. No. 4,323,578, filed Apr. 14, 1980, which is a continuation-in-part application of Patent Application Ser. No. 065,485, filed Sept. 10, 1979 now abandoned.

BACKGROUND OF THE INVENTION

This invention relates to insecticidal carbamates and novel intermediates thereto.

U.S. Pat. No. 3,576,834 discloses insecticidal carbamates of the formula

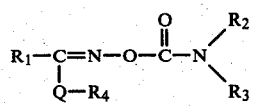

where $R_1$, $R_2$, $R_3$, $R_4$ and Q represent various defined substituents. For preparing these insecticides, the patent discloses starting materials of the formula

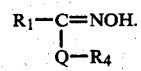

Belgium Pat. BE No. 848,912 discloses symmetrical carbamoylsulfides of the following formula:

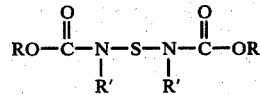

where R and R' represent substituents of varying scope.

Belgium Pat. BE No. 848,913 discloses unsymmetrical carbamoylsulfides of the formula:

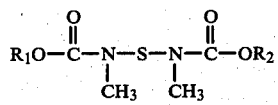

where $R_1$ and $R_2$ represent substituents of varying scope.

L. W. Kissinger, W. E. McQuistion, and M. Swartz, Tetrahedron, 19, 137 (1963) describe the preparation of 2,2,2-trifluoroacetohydroxyamoyl chloride in low yield by the reaction of NOCl with $CF_3CHN_2$.

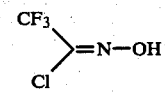

SUMMARY OF THE INVENTION

This invention relates to novel compounds of Formula Ia, to agricultural compositions containing them, to methods of use of these compounds as insecticides:

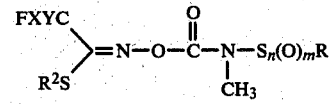

wherein X and Y are independently H or F;

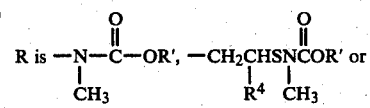

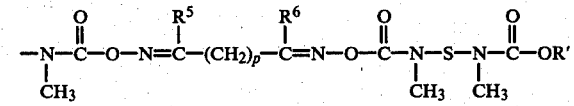

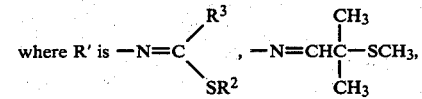

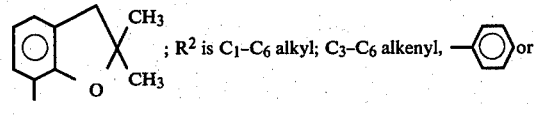

$R^3$ is CFXY, $CON(CH_3)_2$, $CH_2OCH_3$, or $C_1$-$C_3$ alkyl;

$R^4$ is H or $CH_3$;

n is 1 or 2;

m is 0 or 1;

p is 0, 1 or 2;

$R^5$ or $R^6$ are independently H, $C_1$-$C_4$ alkyl, phenyl or phenyl substituted with one atom of F, Cl, Br or $CH_3$;

provided that when:

(1) R is

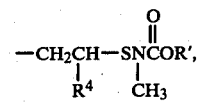

n must be 1;

(2) $R^4$ is $CH_3$, R' must be

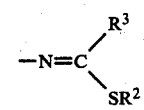

and $R^3$ must be CFXY;

(3) n is 2, m must be 0.

Also, this invention relates to novel compounds of formula Ib, to agricultural compositions containing them, to methods of use of these compounds as insecticides.

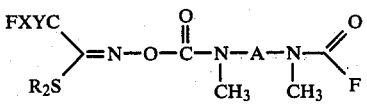 Ib where A is —S—, —S—S—, —S—CH₂CH₂—S—,

or

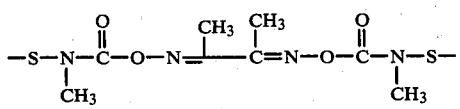

and X, Y and R² are as previously defined in Formula Ia. The compounds of Formula Ib are also useful intermediates in preparing the insecticidal compounds of Formula Ia.

It is understood that formulae Ia and Ib include the isomers of the E and Z configurations about the C=N bond since both isomers of Ia and Ib are active insecticides.

PREFERRED COMPOUNDS

Preferred for their ease of synthesis are those compounds of Formula I wherein n is 1, m is 0, p is 0 and R⁵ and R⁶ are independently H or C₁-C₄ allyl.

More preferred for reasons of high insecticidal activity are those compounds wherein:

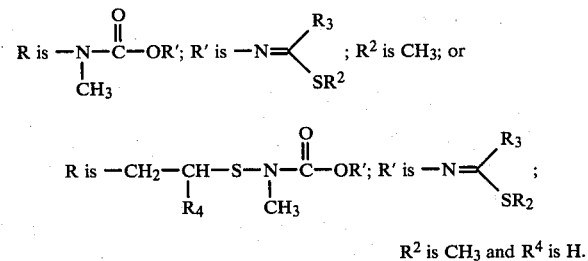

R² is CH₃ and R⁴ is H.

Even more preferred for reasons of higher insecticidal activity, are those compounds of the more preferred wherein:

R³ is CFXY, CON(CH₃)₂, or CH₃.

Most preferred for reasons of even higher insecticidal activity, are those compounds of the even more preferred wherein:

R³ is CF₃, CON(CH₃)₂ or CH₃; and X and Y are F.

Specifically preferred for highest insecticidal activity are the compounds of Formula Ia:

N,N'-[thiobis[(methylimino)carbonyloxy]]bis[2,2,2-trifluoroethanimidothioate acid], dimethyl ester, Z, Z-isomer;

N,N'-[thiobis[(methylimino)carbonyloxy]]bis[2,2,2-trifluoroethanimidothioic acid], dimethyl ester, E, E-isomer;

N,N'-[thiobis[(methylimino)carbonyloxy]]bis[2,2,2-trifluoroethanimidothioic acid], dimethyl ester, E, Z-isomer;

N-[N-[N-(1-(methylthio)ethylideneaminooxycarbonyl)-N-methylaminothio]-N-methylaminocarbonyloxy]-2,2,2-trifluoroethanimidothioic acid, methyl ester; and Dimethyl N,N'-[2,3-butanediylidenebis[nitrilooxycarbonyl-(N-methylimino)thio(N-methylimino)carbonyloxy]]bis[2,2,2-trifluoroethaniminothioate].

Specifically preferred for greatest ease of synthesis and/or insecticidal activity are the compounds of formula Ib where Methyl 2,2,2-trifluoro-N-[N-[N-(fluorocarbonyl)-N-methylaminothio]-N-methylaminocarbonyloxy]-ethanimidothioate;

Methyl 2,2,2-trifluoro-N-[N-[N-(fluorocarbonyl)-N-methylaminosulfinyl]-N-methylaminocarbonyloxy]-ethanimidothioate;

Methyl 2,2,2-trifluoro-N-[N-[N-(fluorocarbonyl)-N-methylaminodithio]-N-methylaminocarbonyloxy]-ethanimidothioate;

Methyl 2,2,2-trifluoro-N-[N-[2-[N-(fluorocarbonyl)-N-methylaminothio]ethylthio]-N-methylaminocarbonyloxy]-ethanimidothioate.

Methyl 2,2,2-trifluoro-N-[N-[N-[[2-[[N-[N-(fluorocarbonyl)-N-methylaminothio]-N-methylamino]-carbonyloxyimino]-1-methylpropylidene]aminooxycarbonyl]-N-methylaminothio]-N-methylaminocarbonyloxy]ethanimidothioate.

PREPARATION

The compounds of Formula Ia in which R is

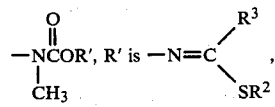

R₃ is CFXY, m is 1, and n is 1 are most readily prepared, as shown in Equation A, by reacting two moles of an acid ester of Formula II with one mole of sulfur monochloride in the presence of an acid acceptor:

Equation A

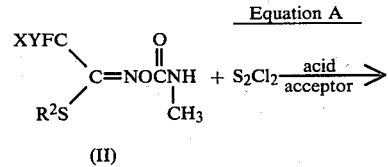

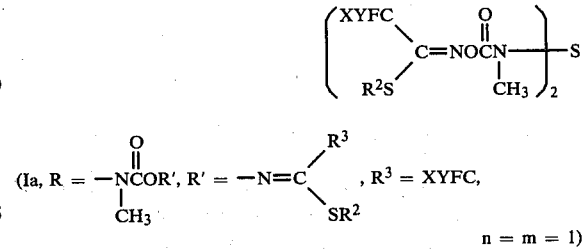

wherein X, Y and R² are as previously defined.

The reaction of Equation A can be carried out in an inert organic solvent such as methylene chloride dioxane, tetrahydrofuran, chloroform, 1,2-dichloroethane, benzene, toluene, or the xylenes. Mixtures of these solvents can also be used.

The acid acceptor used in Equation A can be a tertiary organic amine, such as trimethylamine, triethylamine, N,N-dimethylaniline, or pyridine.

The process can be carried out at a temperature between about −20° C. and 60° C., preferably between about −5° C. and 40° C. Pressure is not critical, for convenience atmospheric pressure is preferred.

The compounds of Formula Ia in which R is

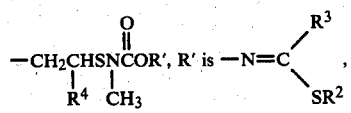

and $R_3$ is XYFC are most readily prepared, as shown in Equation B, by reacting two moles of an acid ester of Formula II with one mole of an alkane disulfenyl halide of Formula III in the presence of an acid acceptor:

Equation B

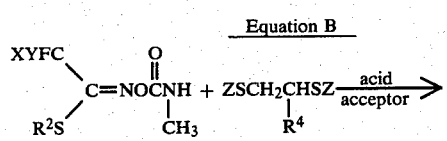

II    III

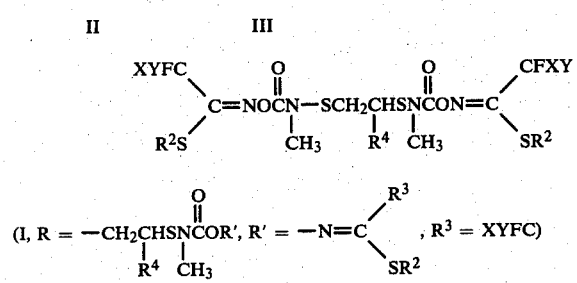

wherein X, Y, $R^2$, and $R^4$ are as previously defined and Z is halogen.

The reaction of Equation B can be carried out in an inert organic solvent such as methylene chloride, dioxane, tetrahydrofuran, chloroform, 1,2-dichloroethane, benzene, toluene, or the xylenes. Mixtures of these solvents may also be used.

The acid acceptor used in Equation B can be a tertiary organic amine, such as trimethylamine, triethylamine, N,N-dimethylaniline, or pyridine.

The process can be carried out at a temperature between about −20° C. and 60° C., preferably between about −5° C. and 40° C. Pressure is not critical, for convenience atmospheric pressure is preferred.

The compounds of Formula Ia in which R is

—NCOR'
|
CH₃ can also be prepared, as shown in Equation C, by reacting one mole of an oxime of Formula IV with Formula IV in the presence of an acid acceptor to afford one mole of the novel carbamoyl fluoride intermediate of Formula VI which is in turn reacted with one mole of R'OH in the presence of an acid acceptor:

Equation C

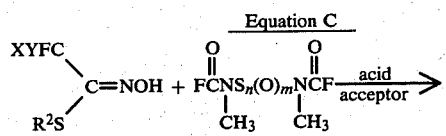

IV    V

-continued
Equation C

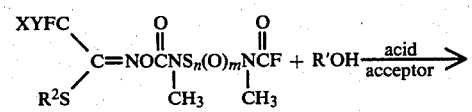

VI

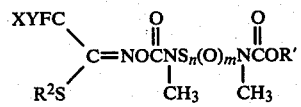

(I, R = 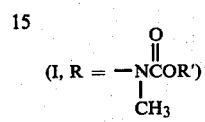)

wherein X, Y, $R^2$, R', n, and m are as previously defined.

The reaction shown in Equation C can be carried out in inert organic solvents such as benzene, toluene, the xylenes, methylene chloride, chloroform, ethylene dichloride, acetone, methyl ethyl ketone, dioxane, tetrahydrofuran, acetonitrile, or dimethylformamide. Mixtures of these solvents may be used. The reaction can be carried out at temperatures between 0° and 100° C., preferably between 20° to 50° C. Pressure is not critical for the reaction procedure since pressures above and below atmospheric are suitable. For convenience, atmospheric pressure is preferred.

The acid acceptor employed in Equation C can be tertiary organic amines, such as trimethylamine, triethylamine, N,N-dimethylaniline, or pyridine, or inorganic bases, such as the alkali metal and alkaline earth metal hydroxides, carbonates, bicarbonates, and alkoxides, such as sodium methoxide or potassium tert-butoxide.

The compounds of Formula Ia in which

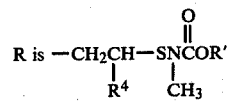

and $R^4$ is H can be prepared, as shown in Equation D, by reacting one mole of an oxime of Formula IV with one mole of a biscarbamoyl fluoride of Formula VII in the presence of an acid acceptor to afford one mole of the novel carbamoyl fluoride intermediate of Formula VIII which is in turn reacted with one mole of R'OH in the presence of an acid acceptor:

Equation D

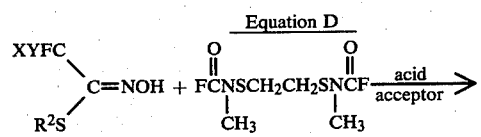

IV    VII

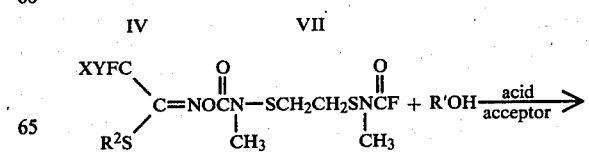

VIII

-continued
Equation D

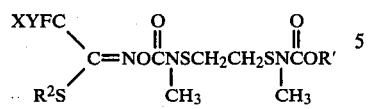

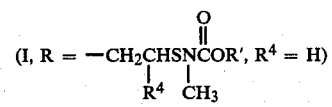

wherein X, Y, R² and R' are as previously defined.

The reaction shown in Equation D can be carried out in inert organic solvents such as benzene, toluene, the xylenes, methylene chloride, chloroform, ethylene dichloride, acetone, methyl ethyl ketone, dioxane, tetrahydrofuran, acetonitrile, or dimethylformamide. Mixtures of these solvents may be used. The reaction can be carried out at temperatures between 0° and 100° C., preferably between 20° and 50° C. Pressure is not critical for the reaction procedures since pressures above and below atmospheric are suitable. For convenience, atmospheric pressure is preferred.

The acid acceptor employed in Equation D can be tertiary organic amines, such as trimethylamine, triethylamine, N,N-dimethylaniline, or pyridine, or inorganic bases, such as the alkali metal and alkaline earth metal hydroxides, carbonates, bicarbonates, and alkoxides, such as sodium methoxide or potassium tert-butoxide.

The compounds of Formula Ia obtained by the reactions described in Equation D can be purified by methods known to those skilled in the art, such as recrystallization, column chromatography or another suitable procedure.

The compounds of Formula Ia in which R is

can also be prepared, as shown in Equation E, by reacting one mole of an oxime or phenol (R'OH) with one mole of a biscarbamoyl fluoride of Formula V in the presence of an acid acceptor to afford one mole of the carbamoyl fluoride intermediate of Formula IX which is in turn reacted with one mole of an oxime of Formula IV in the presence of an acid acceptor:

Equation E

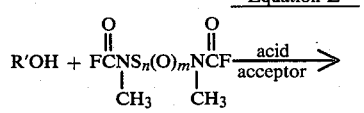

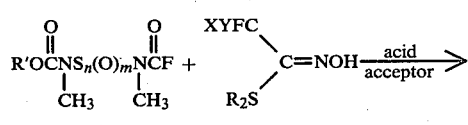

-continued
Equation E

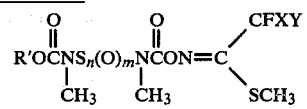

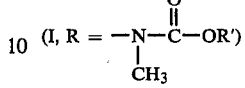

wherein X, Y, R², R', n, and m are as previously defined.

The reactions shown in Equation E can be carried out in inert organic solvents such as benzene, toluene, the xylenes, methylene chloride, chloroform, ethylene dichloride, acetone, methyl ethyl ketone, dioxane, tetrahydrofuran, acetonitrile, or dimethylformamide. Mixtures of these solvents may be used. The reaction can be carried out at temperatures between 0° and 100° C., preferably between 20° to 50° C. Pressure is not critical for the reaction procedure since pressures above and below atmospheric are suitable. For convenience, atmospheric pressure is preferred.

The acid acceptor employed in Equation E can be tertiary organic amines, such as trimethylamine, triethylamine, N,N-dimethylaniline, or pyridine, or inorganic bases, such as the alkali metal and alkaline earth metal hydroxides, carbonates, bicarbonates, and alkoxides, such as, sodium methoxide or potassium tert-butoxide.

The compounds of Formula Ia obtained by the reactions described in Equation E can be purified by methods known to those skilled in the art, such as recrystallization, column chromatography or another suitable procedure.

The compounds of Formula Ia in which R is

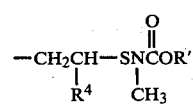

and R⁴ is H can be prepared, as shown in Equation F, by reacting one mole of an oxime or phenol of Formula R'OH with one mole of a biscarbamoyl fluoride of Formula VII to afford one mole of the carbamoyl fluoride intermediate of Formula X which is in turn reacted with one mole of an oxime of Formula IV in the presence of an acid acceptor:

Equation F

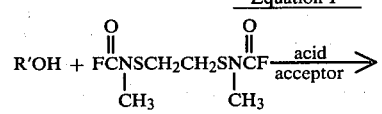

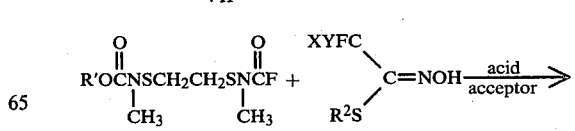

-continued
Equation F

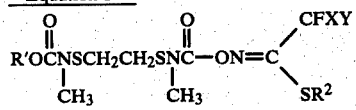

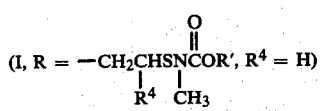

wherein X, Y, $R^2$, R', n and m are as previously defined.

The reactions shown in Equation F can be carried out in inert organic solvents such as benzene, toluene, the xylenes, methylene chloride, chloroform, ethylene dichloride, acetone, methyl ethyl ketone, dioxane, tetrahydrofuran, acetonitrile, or dimethylformamide. Mixtures of these solvents may be used. The reaction can be carried out at temperatures between 0° and 100° C., preferably between 20° to 50° C. Pressure is not critical for the reaction procedure since pressures above and below atmospheric are suitable. For convenience, atmospheric pressure is preferred.

The acid acceptor employed in Equation F can be tertiary organic amines, such as trimethylamine, triethylamine, N,N-dimethylaniline, or pyridine, or inorganic bases, such as the alkali metal and alkaline earth metal hydroxides, carbonates, bicarbonates, and alkoxides, such as sodium methoxide or potassium tert-butoxide.

Compounds where R is:

The acid esters of Formula II can be prepared by the reaction of methyl isocyanate with the appropriate oxime as described in U.S. Pat. No. 3,576,834.

For the compounds of Formula III, chlorine is the preferred halogen for economic reasons, and these compounds can be prepared by a suitable modification of the method described for preparing ethane-1,2-disulfenyl chloride in *Journal of Heterocyclic Chemistry*, 6, 629 (1969). Alkane sulfenyl halides such as those of Formula III wherein Z is fluorine, bromine, or iodine are also known and may be prepared by the methods reviewed in *Synthesis*, 11, 561–580 (1970).

The compound of Formula V in which n is 1 and m is 0 can be prepared from N-methyl carbamoyl fluoride and sulfur monochloride as described in German DT No. 2,654,246 and Belgian BE No. 848,914.

The compound of Formula V in which n is 2 and m is 0 can be prepared from N-methyl carbamoyl fluoride and sulfur monochloride as described in German DT No. 1,297,095.

The compound of Formula V in which n is 1 and m is 1 and its method of preparation are as follows:

Thio bis-carbamoyl fluorides (described in Belgian Pat. No. 717,705) are treated with at least one equivalent of an appropriate oxidizing agent, such as m-chloroperbenzoic acid or peracetic acid. The reaction is carried out at a temperature between −10° to +60° C., in a suitable solvent, such as methylenechloride or chloroform. After a reaction time of 0.5 to 72 hours, the reaction mixtures contain compounds of formula Ia.

The compound of Formula VII and its method of

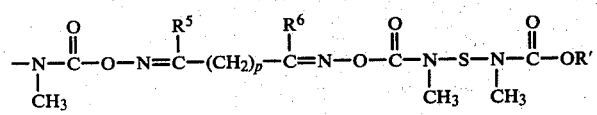

are obtained by the procedure of Equation G:

EQUATION G

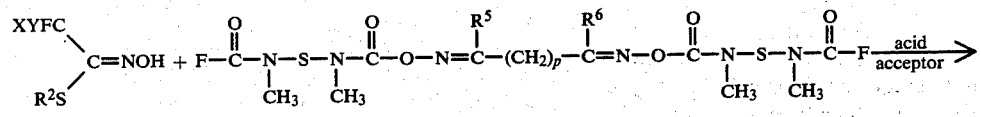

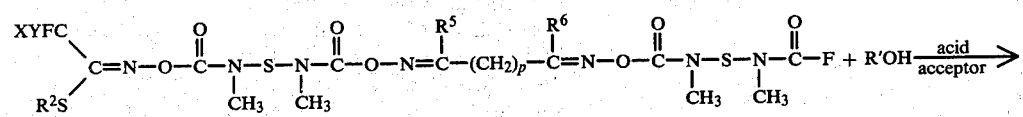

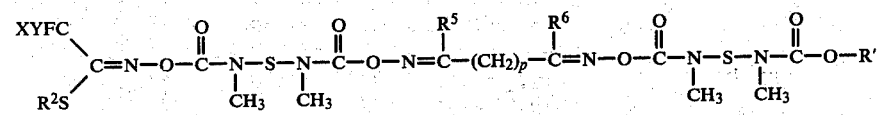

This equation is substantially the same process as in Equation D discussed above except for the above definition of R and the bis-carbamoyl fluoride intermediate VII has formula B.

The compounds of Formula Ia obtained by the reactions described in Equation F can be purified by methods known to those skilled in the art, such as recrystallization, column chromatography or another suitable procedure.

preparation are claimed and disclosed in U.S. Pat. No. 4,127,605.

The oximes of formula IV having the Z-configuration (with S and O atoms cis to one another) are prepared by the reaction of the sodium salt of a thiol ($R^2SNa$) with a acetohydroxamoyl chloride of formula XI or a O-(trifluoroacetyl)hydroxamoyl chloride of formula XII in methanol or other suitable alcohol solvent.

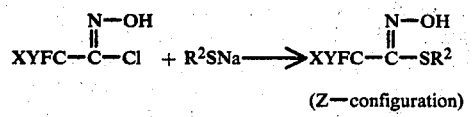

(Z—configuration)

XI            IV

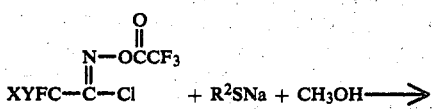

(Z—configuration)

IV

The O-(trifluoroacetyl)acetohydroxamoyl chlorides of formula XII, along with dioxazoles of formula XIII, are prepared by heating mixtures of PCl₅ with diacylhydroxylamine of formula XIV, and then separating the products by distillation.

XIV

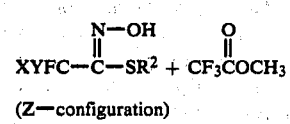

XII        XIII

The acetoydroxamoyl chlorides of formula XI are prepared by reaction of O-(trifluoroacetyl)-acetohydroxamoyl chlorides of formula XII with a suitable alcohol, such as methanol, and separating the products by distillation.

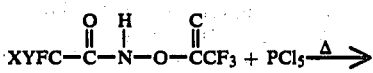

XII

XI

The oxime of formula IV having the E-configuration (with X and O atoms cis to one another) are prepared by reacting, preferably at a low temperature (0° to −100°), a dioxazole of formula XII with a solution of the sodium salt of a thiol, R²SNa, in methanol or other alcohol solvent.

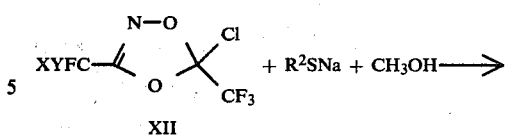

XII

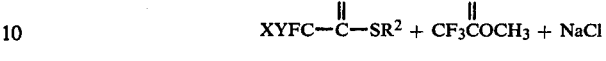

(E—configuration)

IV

Alternatively, mixtures of the E and Z-forms of compound IV can be prepared by irradiating either pure isomer with ultraviolet light until a photostationary state is obtained.

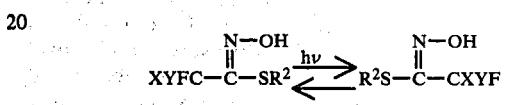

IV (Z—form)      IV (E—form)

In the following examples, all parts are by weight and temperatures are in degrees Centigrade unless otherwise specified.

EXAMPLE 1

N,N'-[Thiobis[(methylimino)carbonyloxy]]bis[2,2,2-trifluoroethanimidothioic acid], dimethyl ester

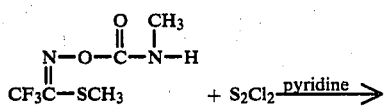

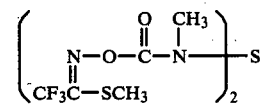

A solution of 6.75 g (0.05 mol) of freshly distilled sulfur monochloride in 50 ml of dichloromethane was added dropwise to a stirred mixture of 21.62 g (0.1 mol) of S-methyl 2,2,2-trifluoro-N-(methylcarbamoyloxy)-thioacetimidate and 9.49 g (0.12 mol) of pyridine cooled to 0°. The mixture was stirred for 3 hours at 0°, and then warmed to room temperature (25°) and stirred for 17 hours. The reaction mixture was poured into water, and the aqueous mixture was extracted with dichloromethane. The extracts were washed with water, dried (MgSO₄), and then evaporated to dryness under reduced pressure. The residue was recrystallized from heptane to give 11.8 g (51%) of N,N'-[thiobis[(methylimino)carbonyloxy]]bis[2,2,2-trifluoroethanimidothioic acid], dimethyl ester, as colorless needles: mp 126°-127°; ir (KBr) 5.70μ (C=O), 6.40μ (C=N); ¹H NMR (CDCl₃) δ 2.62 ppm (q, J=1.4 Hz, 6H) and 3.53 ppm (s, 6H); ¹⁹F NMR (CDCl₃) δ −63.8 ppm (q, J=1.4 Hz). Anal. Calcd. for C₁₀H₁₂F₆N₄O₄S₃: C, 25.97; H, 2.62; F, 24.65; N, 12.12; S, 20.80. Found: C, 26.00; H, 2.54; F, 24.71; N, 12.11; S, 21.28.

The Z and E isomers of the intermediate used above can be prepared as follows:

A. S-Methyl (Z)-2,2,2-trifluoro-N-(methylcarbamoyloxy)thioacetimidate

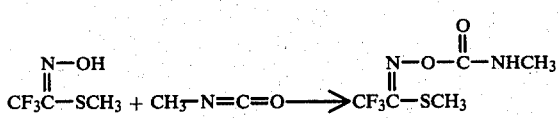

A mixture of 17.12 g (0.3 mol) of methyl isocyanate and 47.74 g (0.3 mol) of S-methyl (Z)-2,2,2-trifluoro-N-(hydroxy)thioacetimidate was sealed in a glass tube and heated at 100° in a steam bath for 17 hours. The contents of the tube were distilled at reduced pressure to give 62.02 g (96%) of S-methyl (Z)-2,2,2-trifluoro-N-(methylcarbamoyloxy)thioacetimidate as a colorless, viscous liquid: bp 96° (0.6 mm); $n_D^{25}$ 1.4638; ir (neat) 5.73μ (C=O); $^{19}$F NMR (CFCl$_3$) δ −64.6 ppm (q, J=1.2 Hz); $^1$H NMR (CFCl$_3$) δ 2.63 ppm (q, J=1.2 Hz, 3), 2.88 ppm (d, J=4.5 Hz, 3H) and 6.47 ppm (NH).

Anal. Calcd. for C$_5$H$_7$F$_3$N$_2$O$_2$S: C, 27.78; H, 3.27; F, 26.36; N, 12.96; S, 14.83. Found: C, 27.69; H, 3.36; F, 26.52; N, 12.87; S, 14.82.

B. S-Methyl (E)-2,2,2-trifluoro-N-(methylcarbamoyloxy)-thioacetimidate

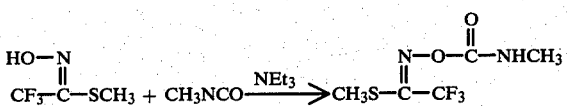

One drop of triethylamine was added to a mixture of 6.37 g (0.04 mol) of S-methyl (E)-2,2,2-trifluoro-N-hydroxythioacetimidate and 2.28 g (0.04 mol) of methyl isocyanate. An exothermic reaction ensued, and the reaction mixture was cooled in an ice-bath. The reaction mixture solidified on cooling. Recrystallization from ether gave 6.39 g (74% yield) of S-methyl (E)-2,2,2,-trifluoro-N-(methylcarbamoyloxy)thioacetimidate as colorless crystals, mp. 83°–85°. Analysis of the isomer prepared in a similar procedure follows:

ir (KBr) 5.77μ (C=O), 6.40μ (C=N); $^{19}$F NMR (CDCl$_3$) δ −65.9 ppm (s); $^1$H NMR (CDCl$_3$) δ 2.50 ppm (s, 3H), 2.92 ppm (d, J=4 Hz, 3H) and 5.65 ppm (NH).

Anal. Calcd. for C$_5$H$_7$F$_3$N$_2$O$_2$S: C, 27.78; H, 3.27; N, 12.96. Found: C, 28.06; H, 3.38; N, 13.01.

The hydroxy intermediate isomers used in (A) and (B) are provided by the following:

C. S-Methyl (E)-2,2,2-Trifluoro-N-hydroxythioacetimidate

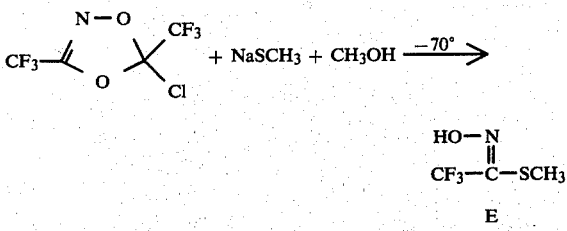

Methanethiol, 28 ml (0.56 mol) was distilled into a solution prepared by dissolving 9.2 g (0.4 mol) of sodium in 300 ml of methanol. The reaction mixture was cooled to −70°, and 97.4 g (0.4 mol) of 2-chloro-2,5-bis(trifluoromethyl)-1,3,4-dioxazole was added dropwise, keeping the temperature at −70° or below. The reaction mixture was warmed to 25° and stirred for 18 hours, and then filtered to remove the suspended NaCl. The filtrate was evaporated to dryness under reduced pressure, and the residue was fractionally sublimed at 50° and 5 mm pressure. The first fraction, 5.21 g (8% yield) consisted of a mixture containing 78% E-isomer and 22% Z-isomer. The second fraction, 43.71 g (69% was 99+% E-isomer of 2,2,2-trifluoro-N-hydroxythioacetimidate, mp 60°–62° (analysis by $^{19}$F NMR).

These isomers can be separated by distillation. The E-isomer is lower-boiling: bp 112°–113° (200 mm); mp 52°–55°; $^{19}$F NMR (CDCl$_3$) δ −66.2 ppm (s); $^1$H NMR δ2.37 ppm (s). The Z-isomer is higher boiling; bp 124°–125° (200 mm). Prolonged heating converts the E-isomer to the Z-isomer. Much of the E-isomer was isomerized during the distillation.

2-Chloro-2,5-bis(trifluoromethyl)-1,3,4-dioxazole was obtained as follows:

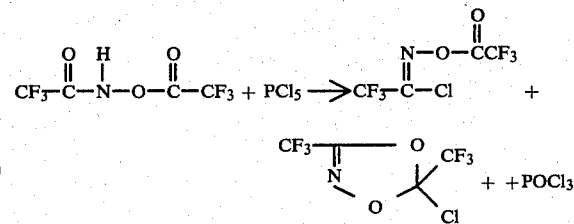

A mixture of 433 g (1.92 mol) of curde N, O-bis(trifluoroacetyl)hydroxylamine and 433 g (2.08 ml) of phosphorus pentachloride was gently heated under a reflux condenser cooled to −78° with solid carbon dioxide-acetone until the mixture liquified and evolution of HCl ceased. Distillation gave 49.28 g (11%) of 2-chloro-2,5-bis(trifluoromethyl)-1,3,4-dioxazole as a colorless liquid: bp 52°–53°; $n_D^{25}$ 1.3000; ir (liquid) 6.02μ (C=N); $^{19}$F NMR CCl$_3$F) δ−68.0 ppm (s, 3F) and −82.4 ppm (s, 3F); and 271.51 g (58%) of 2,2,2-trifluoro-O-(trifluoroacetyl)acetohydroxamoyl chloride as a colorless liquid: bp 83°–84°; $n_D^{25}$ 1.3272; ir (liquid) 6.12μ (C=N) and 5.41μ (C=O); $^{19}$F NMR (CCl$_3$F) δ70.0 ppm (s, 3F) and −74.1 ppm (s, 3F).

Anal. Calcd. for C$_4$ClF$_6$NO$_2$: C, 19.73; Cl, 14.56; F, 46.82; N, 5.75. Found (dioxazole): C, 19.95; Cl, 14.07; F, 46.57; N, 5.68. Found (hydroxamoyl chloride): C, 19.50; Cl, 14.87; F, 46.68; N, 5.87.

Trifluoroacetohydroxamoyl chloride was prepared from the trifluoroacetyl derivative as follows:

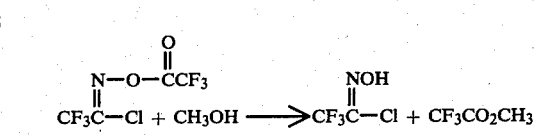

Methanol, 21.0 g (0.65 mol) was added dropwise to 153 g (0.65 mol) of 2,2,2-trifluoro-O-(trifluoroacetyl)acetohydroxamoyl chloride cooled to 0°. The reaction mixture was allowed to warm to 25° and then distilled to give methyl trifluoroacetate, bp 44°, and then 84.8 g (91%) of trifluoroacetohydroxamoyl chloride as a colorless liquid: bp 90°–91°; ir (liquid) 6.11μ (C=N); $^{19}$F NMR (CFCl$_3$) δ−70.1 ppm (s).

Anal. Calcd. for $C_2HClF_3NO$: C, 16.28; H, 0.69; Cl, 24.04; F, 38.64; N, 9.50. Found: C, 16.38; H, 0.98; Cl, 24.18; F, 38.77; N, 9.51.

D. Isomerization of 2,2,2-Trifluoro-N-hydroxythioacetimidate by Irradiation with Ultraviolet Light

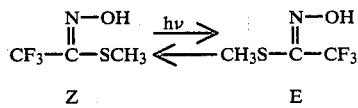

A 6% solution of (Z)-2,2,2-trifluoro-N-hydroxythioacetimidate in $CDCl_3$ was irradiated through a water-cooled quartz filter with a Hanovia ® 450-watt medium pressure mercury arc lamp. After 2 hrs of irradiation, a photostationary state containing 27% E-isomer and 73% Z-isomer was reached, as indicated by $^{19}F$ NMR analysis.

A 6% solution of the E-isomer in $CDCl_3$ was irradiated under the same conditions to give the same photostationary state in 20 minutes.

E. S-Methyl (Z)-2,2,2-Trifluoro-N-hydroxythioacetimidate

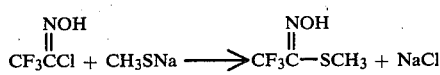

Methanethiol, 38 ml (measured at 0°, 0.68 mol) was distilled into a solution prepared by dissolving 14.7 g (0.638 g- atom) of sodium in 260 ml of methanol. The resulting solution was cooled to 0°, and 94.1 g (0.638 mol) of trifluoroacetohydroxamoyl chloride was added dropwise, keeping the temperature below 10°. The reaction mixture was stirred at room temperature for 3 days, filtered to remove NaCl, and evaporated to dryness under reduced pressure. (Care should be taken to avoid loss of product due to sublimation). The residue was sublimed at 50°–60° and 0.5 mm pressure to give 84.71 g (83%) of S-methyl (Z)-2,2,2-trifluoro-N-hydroxythioacetimidate as large, colorless crystals, mp 52°–54°. A sample prepared in a similar way was analyzed: ir (KBr) 3.05μ (OH) and 6.22μ (C=N; $^1H$ NMR ($CDCl_3$) δ2.53 ppm (m, 3H) 8.07 ppm (s, 1H); $^{19}F$ NMR ($CDCl_3$) δ−66.6 ppm (q, J=1 Hz). An X-ray crystal structure analysis showed the compound to have a Z configuration, with the S and O atoms cis to one another.

Anal. Calcd. for $C_3H_4F_3NOS$: C, 22.64; H, 2.53; F, 35.82; N, 8.80; S, 20.15. Found: C, 22.65; H, 2.40; F, 35.73; N, 8.85; S, 20.47.

N,N′-thiobis[N-methylcarbamoyl fluoride] (11.97 g) and 19.13 g of S-methyl (Z)-2,2,2-trifluoro-N-hydroxythioacetimidate with 13.15 g of triethylamine in 175 ml of tetrahydrofuran at 25° after 2.5 hours gave 21.36 g of dimethyl N,N′-[thiobis(methylimino)carbonyloxy]]-bis[2,2,2-trifluoroethanimidothioate], Z,Z-isomer, as colorless crystals, mp 126°–127°.

A similar reaction of 72% E isomer and 28% Z isomer of the trifluorohydroxy thioacetimidate was followed by TLC. It was completed after 30 minutes, with the formation of 3 new products. The reaction mixture was evaporated to dryness under reduced pressure, and the solid residue was washed with water. There was obtained 12.56 g (95%) of a white crystalline solid. Analysis by high pressure liquid chromatography on silica (eluted with 2.5% EtOAc in BuCl) indicated the product consisted of a mixture containing 9% Z,Z-isomer, 42% E,Z-isomer and 49% E,E-isomer. The mixture was separated into its components by HPLC on silica, with elution by EtOAc/BuCl. The Z,Z-isomer was eluted first, the E,E-isomer was eluted second, and the E,Z-isomer was eluted last.

The E,E-isomer was obtained as a colorless crystalline solid; mp 99°–101° (after recrystallization from butyl chloride); $^{19}F$ NMR ($CDCl_3$) δ−66.0 ppm (s); $^1H$ NMR ($CDCl_3$) δ2.57 ppm (s, 6H), 3.49 ppm (s, 6H); ir (KBr) 5.65μ (C=O), 6.38 (C=N).

Anal. Calcd. for $C_{10}H_{12}F_6N_4O_4S_3$: C, 25.97; H, 2.62; N, 12.12. Found: C, 26.08; H, 2.83; N, 12.06.

The E,Z-isomer was obtained as a colorless crystalline solid: mp 106°–108° (after recrystallization from heptane); $^{19}F$ NMR ($CDCl_3$) δ−63.7 ppm (q, J=1.4 Hz 3F), −66.0 ppm (s, 3F); $^1H$ NMR ($CDCl_3$) δ2.55 ppm (s, 3H), 2.61 ppm (q, J=1.4 Hz, 3H), 3.51 ppm (s, 6H); ir (KBr) 5.69 and 5.76μ (C=O), 6.41μ (C=N).

Anal. Calcd. for $C_{10}H_{12}F_6N_4O_4S_3$: C, 25.97; H, 2.62; N, 12.12. Found: C, 26.33; H, 2.68; N, 12.13.

By the process of Example 1, other N-(methylcarbamoyloxy)thioacetimidates are converted to the corresponding thiobis compounds as described in Equation A. The thioacetimidates of the formula

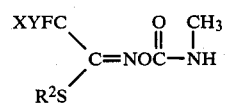

are obtained by reaction of methyl isocyanate with substantially equivalent amounts of S-substituted fluorinated N-hydroxythioacetimidate of the formula

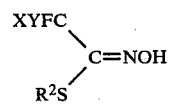

where X, Y and $R^2$ are as previously defined and the isomer is Z and/or E configuration. The reaction is effected in inert solvent such as halogenated methane, at about room temperature. The following table shows compounds obtained by this procedure.

TABLE 1

| | | | | Analysis (Found) | | |
|---|---|---|---|---|---|---|
| X | Y | $R^2$ | mp or bp °C. | C | H | N |
| H | H | $CH_3$ | mp 53–56 | 33.21 | 4.87 | 15.69 |
| F | F | $C_2H_5$ | bp 116–8/0.3 mm | 31.63 | 4.10 | — |
| F | F | $C_3H_{7n}$ | bp 115–7/0.2 mm | 34.70 | 4.82 | 11.44 |
| F | F | $C_3H_{7(iso)}$ | mp 75–7 | 34.19 | 4.45 | 11.31 |
| F | F | $C_4H_{9(t)}$ | bp 113–5/0.2 mm | 37.37 | 5.21 | 10.58 |
| F | F | $CH_2CH=CH_2$ | bp 117–9/0.2 mm | 34.41 | 3.91 | 11.75 |
| F | F | $C_6H_5$ | mp 88–90 | 42.99 | 3.19 | 9.95 |

EXAMPLE 2

Methyl 2,2,2-Trifluoro-N-[N-[N-(fluorocarbonyl)-N-methylaminothio]N-methylaminocarbonyloxy]ethanimidothioate Triethylamine (2.22 g, 0.22 mol) were added dropwise with stirring to a solution of 3.86 g (0.21 mol) of N,N'-thiobis[N-methylcarbamoyl fluoride] and 2.94 g (0.20 mol) of methyl 2,2,2-trifluoro-N-hydroxyethanimidothioate in 25 ml of tetrahydrofuran at 20°–25°. After the addition was complete the reaction mixture was stirred for 18 hours at ambient temperature. Solvent was evaporated with a vacuum pump to leave a beige powder which was dissolved in 30 ml of methylene chloride. The solution was washed with water; the organic phase was dried with MgSO$_4$, filtered and evaporated to dryness to give 5.49 g of a beige powder. The powder was recrystallized from 35 ml of chlorobutane. The solid was filtered and the filtrate evaporated to give a tan syrupy residue which contained methyl 2,2,2-trifluoro-N-[N-[N-(fluorocarbonyl)-N-methylaminothio]N-methylaminocarbonyloxy]ethanimidothioate.

The latter compound corresponds to compound VI of Equation C where X=Y=F, R$^2$=CH$_3$, n=1 and m=0. Reaction with R'OH gives compounds of formula I where R is

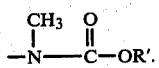

EXAMPLE 3

N,[N-[N-(1-(Methylthio)ethylidenaminooxycarbonyl)-N-methylaminothio]-N-methylaminocarbonyloxy]-2,2,2-trifluoroethanimidothioic acid, methyl ester A solution of 1.47 g (10 mmol) of S-Methyl 2,2,2-trifluoro-N-(hydroxy)thioacetimidate and 2.63 g (9.8 mmol) of N-[N-[N-methyl-N-(fluorocarbonyl)aminothio]-N-methylaminocarbonyloxy]ethaneimidothioic acid methyl ester in 25 ml of tetrahydrofuran was treated dropwise with 1.11 g (1.53 ml, 11 mmol) of triethylamine and allowed to stir at room temperature for 18 hours. The solvent was evaporated at reduced pressure to give a white powder. This solid was then dissolved in 20 ml of methylene chloride and washed with 20 ml of water. The organic phase was separated, dried over magnesium sulfate and evaporated to dryness at reduced pressure to give 3.02 g (75%) of the crude product as a white powder. Recrystallization from 27 ml of chlorobutane gave 2.43 g (61%) of N-[N-[N-[2-dimethylamino)-1-(methylthio)-2-oxoethylidineaminooxycarbonyl]-N-methylaminothio]-N-methylaminocarbonyloxy]-2,2,2-trifluoroethaneimidothioic acid, methyl ester: $^1$H NMR (CDCl$_3$): δ3.53 ppm (s, N-CH$_3$); δ3.50 (s, N-CH$_3$); δ2.62 (q, J≅1.5 Hz; S-CH$_3$ on C-CF$_3$); δ2.42 (s, S-CH$_3$ on C-CH$_3$); δ2.32 (s, C-CH$_3$). $^{19}$F NMR (CDCl$_3$) δ−63.74 ppm (z, J$_{F-H}$≅1.5 Hz). m.p. 111°–112°.

Anal. Calcd. for C$_{10}$H$_{15}$N$_4$O$_4$S$_3$F$_3$: C, 29.40; H, 3.70; N, 13.72. Found: C, 29.26; H, 3.69; N, 13.54.

Compounds which can be prepared by the processes of the Examples and of Equations A-F are listed in Tables I-III.

EXAMPLE 4

Diethyl N,N'[thiobis[(methylimino)carbonyloxy]]-bis[2,2,2-trifluoroethanimidothioate], Z,Z-Isomer

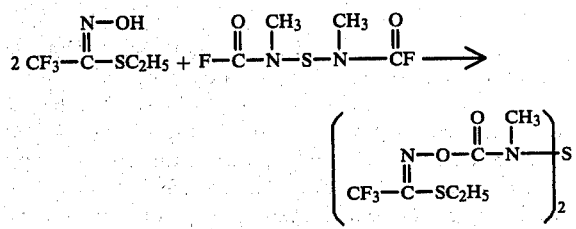

A solution of 3.0 g (0.0296 mol) of triethylamine in 5 ml tetrahydrofuran was added dropwise to a stirred solution of 2.5 g (0.0136 mol) of N,N'-thiobis[N-methylcarbamoyl fluoride] and 5.09 g (0.0296 mol) of S-ethyl (Z)-2,2,2-trifluoro-N-hydroxythioacetimidate in 25 ml tetrahydrofuran cooled to 0°. The reaction mixture was allowed to warm to 25°, stirred 18 hours and then evaporated to dryness under reduced pressure. The residue was broken up, washed thoroughly with water (5.67 g, 85% crude yield), and recrystallized from heptane to give 3.46 g (52%) of diethyl N,N'[thiobis[(methylimino)carbonyloxy]]bis[2,2,2-trifluoroethanimidothioate] as colorless crystals: mp 94°–96°; $^{19}$F NMR (CDCl$_3$) δ−64.0 ppm (s); $^1$H NMR (CDCl$_3$) δ1.38 ppm (t, J=7 Hz, 6H), 3.23 ppm (q, J=7 Hz, 4H), 3.56 ppm (s, 6H).

Anal. Calcd. for C$_{12}$H$_{16}$F$_6$N$_4$O$_4$S$_3$: C, 29.38; H, 3.29; F, 23.24; N, 11.42. Found: C, 29.30; H, 3.18; F, 23.88; N, 11.60.

The S-ethyl (Z)-2,2,2-Trifluoro-N-hydroxythioacetimidate used above was prepared as follows:

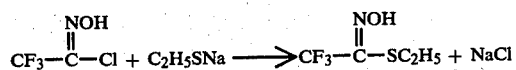

Ethanethiol, 26 ml (0.35 mol) was added dropwise to a solution prepared by dissolving 6.9 g (0.3 mol) of sodium in 100 ml methanol. The reaction mixture was cooled to 0°, and 44.25 g (0.3 mol) of trifluoroacetohydroxamoyl chloride was added dropwise. The reaction mixture was warmed to 25°, stirred for 16 hours, filtered to remove NaCl, and then distilled to give 40.62 g (78%) of (Z)-2,2,2-trifluoro-N-hydroxythioacetimidate as a colorless liquid, bp 64° (4 mm), that solidified to a colorless solid: mp 29°–30°; ir (melt) 6.26μ (C=N); $^{19}$F NMR (CCl$_3$F) δ−66.0 ppm (s); $^1$H NMR (CCl$_3$F) δ1.33 ppm (t, J=7 Hz, 3H), 3.17 ppm (q, J=7 Hz, 2H), 10.0 ppm (OH).

Anal. Calcd. for C$_4$H$_6$F$_3$NOS: C, 27.74; H, 3.49; F, 32.92; N, 8.09; Found: C, 27.83; H, 3.64; F, 32.96; N, 8.23

EXAMPLE 5

Dimethyl N,N'-[thiobis[(methylimino)-carbonyloxy]]bis[2-fluoroethanimidothioate]

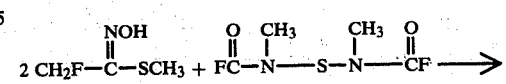

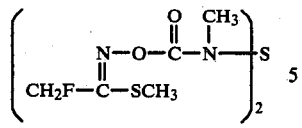

A solution of 3.37 g (0.0185 mol) of triethylamine in 10 ml tetrahydrofuran was added dropwise to a stirred solution of 3.41 g (0.0185 mol) of N,N'-thiobis[N-methylcarbamoyl fluoride] and 4.14 g (0.034 mol) of S-methyl 2-fluoro-N-hydroxy thioacetimidate in 40 ml of tetrahydrofuran at 25°. The mixture was stirred for 16 hours, during which time a precipitate formed. The precipitate was collected on a filter and washed with tetrahydrofurna to give 3.44 g of white crystals. An additional 1.36 g was obtained by evaporation of the filtrate to dryness and washed the residue with water and ether (crude yield, 72%). Recrystallization from chlorobutane gave 2.68 g of dimethyl N,N'[thiobis[(methylimino)carbonyloxy]]-bis[2-fluoroethanimidothioate] as colorless crystals: mp 144°-146°; ir (KBr) 5.74μ (C=O), 6.36μ (C=N); $^{19}$F NMR (DMSO$_{d6}$) δ−217.4 ppm (t, J=46 Hz); $^1$H NMR (DMSO$_{d6}$) δ2.60 ppm (s, 6H), 3.41 ppm (s, 6H), 5.41 ppm (d, J=46 Hz, 4H).

Anal. Calcd. for C$_{10}$H$_{16}$F$_2$N$_4$O$_4$S$_3$: C, 30.76; H, 4.13; N, 14.35. Found: C, 30.96; H, 4.20; N, 14.17.

The S-methyl 2-fluoro-N-hydroxythioacetimidate used above was obtained as follows:

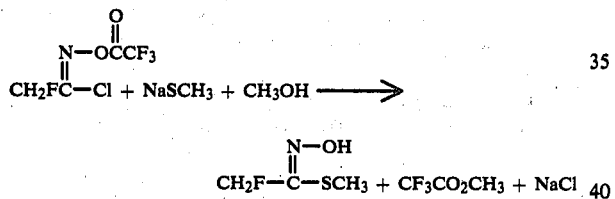

Methanethiol, 10 ml (0.2 mol), was distilled into a solution prepared by dissolving 1.68 g (0.073 mol) of sodium in 50 ml methanol. The reaction mixture was cooled to −10°, and 15.15 g (0.073 mol) of 2-fluoro-O-trifluoroacetylacetohydroxamoyl chloride was added dropwise. The reaction mixture was allowed to warm to 25°, filtered to remove the precipitated salts, and the filtrate was distilled to give 5.75 g (64%) of S-methyl 2-fluoro-N-hydroxythiolacetimidate as a viscous liquid, bp 70°-73° (0.6 mm) that solidified to a colorless solid: mp 52°-55°; $^{19}$F NMR (CDCl$_3$) δ−214.5 ppm (t, J=47 Hz); $^1$H NMR (CDCl$_3$) δ2.48 ppm (s, 3H), 5.13 ppm (d, J=47 Hz, 2H) and 9.20 ppm (OH).

Anal. Calcd. for C$_3$H$_6$FNOS: C, 36.03; H, 4.91; F, 15.43; N, 11.38; S, 26.04. Found: C, 35.97; H, 5.01; F, 15.37; N, 11.47; S, 25.89.

EXAMPLE 6

Di-(1-methylethyl) N,N'-[thiobis[(methylimino)-carbonyloxy]]bis[2,2,2-trifluoroethanimidothioate]

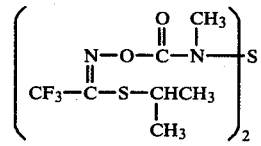

Triethylamine, 4.05 g (0.04 mol), was added dropwise to a solution of 7.47 g (0.04 mol) of S-(1-methylethyl) (Z)-2,2,2-trifluoro-N-hydroxythioacetimidate and 3.69 g (0.02 mol) of N,N'-thiobis[N-methylcarbamoyl fluoride] in 50 ml tetrahydrofuran cooled to 0°. The reaction mixture was allowed to warm to 25°, stirred for 2 hours, and then evaporated to dryness under reduced pressure. The residual oil was taken up in CCl$_3$F, washed with water, dried (MgSO$_4$) and evaporated to dryness to give 8.88 g (86%) of di-(1-methylethyl) N,N'-[thiobis[(methylimino)carbonyloxy]]bis[2,2,2-trifluoroethanimidothioate] as a light yellow glass: ir (neat) 5.68μ (C=O); $^{19}$F NMR (CDCl$_3$) δ−64.7 ppm (s); $^1$H NMR (CDCl$_3$) δ1.40 ppm (d, J=7 Hz, 12H), 3.54 ppm (s, 6H), 4.01 ppm (sept., J=7 Hz, 2H).

Anal. Calcd. for C$_{14}$H$_{20}$F$_6$N$_4$O$_4$S$_3$: C, 32.43; H, 3.89; N, 10.81. Found: C, 32.13; H, 3.71; N, 10.31.

The S-(1-methylethyl) (Z)-2,2,2-trifluoro-N-hydroxythioacetimidate used above was prepared as follows:

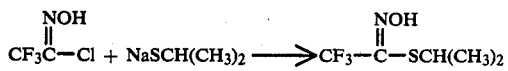

2-Propanethiol, 7.62 g (0.1 mol), was added dropwise to a solution prepared by dissolving 2.07 g (0.09 mol) of sodium in 40 ml of methanol. The reaction mixture was cooled to 0°, and 13.28 g (0.09 mol) of trifluoroacetohydroxamoyl chloride was added dropwise. The reaction mixture was allowed to warm to 25°, stirred for 18 hours, and then filtered to remove NaCl. The filtrate was concentrated under reduced pressure, redissolved in ether, filtered again, and then distilled to give 10.72 g (64%) of S-(1-methyl) (Z)-2,2,2-trifluoro-N-hydroxythioacetimidate as a colorless liquid; bp 51°-52° (2.0 mm); $^{19}$F NMR (CDCl$_3$) δ−67.3 ppm (s); $^1$H NMR (CDCl$_3$) δ1.32 ppm (d, J=7 Hz, 6H), 4.10 ppm sept., J=7 Hz, 1H) and 9.60 ppm (OH).

Anal. Calcd. for C$_5$H$_8$NOS: C, 32.08; H, 4.31; F, 30.53; N, 7.48. Found: C, 32.32; H, 4.27; F, 30.48; N, 7.51.

EXAMPLE 7

Dipropyl N,N'-[thiobis[methylimino)carbonyloxy]]-bis[2,2,2-trifluoroethanimidothioate]

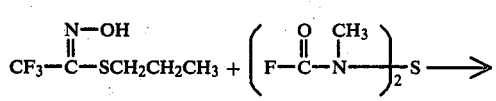

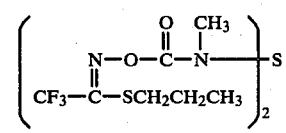

Triethylamine, 6.12 mol (0.04 mol), was added dropwise to a solution of 7.48 g (0.04 mol) of S-propyl (Z)-

2,2,2-trifluoro-N-hydroxythioacetimidate and 3.68 g (0.02 mol) of N,N'-thiobis[N-methylcarbamoyl fluoride] in 50 ml of tetrahydrofuran. The reaction mixture was stirred for 2.5 hours, evaporated to dryness, and then taken up in CH$_2$Cl$_2$ and washed with water, dried (MgSO$_4$) and evaporated again. There was obtained 8.50 g of dipropyl N,N'-[thiobis[(methylimino)carbonyloxy]]-bis[2,2,2-trifluoroethanimidothioate] as a viscous, yellow syrup: n$_D^{25}$ 1.4880; $^{19}$F NMR (CDCl$_3$) δ−63.9 ppm (s); $^1$H NMR (CDCl$_3$) δ1.08 ppm (t, 6H), 1.68 (m, 4H), 3.17 ppm (t, 2H), 3.55 ppm (s, 6H).

The S-propyl (Z)-2,2,2-trifluoro-N-hydroxythioacetimidate used above was prepared as follows:

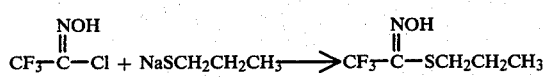

1-Propanethiol, 15.23 g (0.2 mol), was added dropwise to a solution prepared by dissolving 4.14 g (0.18 mol) of sodium in 60 ml methanol. The reaction mixture was cooled to 0° and 26.55 g (0.18 mol) of trifluoroacetohydroxamoyl chloride was added dropwise. The reaction mixture was allowed to warm to 25° and stirred for 18 hours, filtered to remove NaCl, and then distilled to give 28.93 g (86%) of S-propyl (Z)-2,2,2-trifluoro-N-hydroxythioacetimidate as a colorless liquid; bp 61° (1.4 mm); $^{19}$F NMR (CDCl$_3$) δ−65.7 ppm (s); $^1$H NMR δ1.02 ppm (t, J=7 Hz, 3H), 1.62 ppm (m, 2H), 3.10 ppm (t, J=7 Hz, 2H) and 9.82 ppm (OH).

Anal. Calcd. for C$_5$H$_8$F$_3$NOS: C, 32.08; H, 4.31, F, 30.45; N, 7.48; S, 17.13. Found: C, 32.04; H, 4.42; F, 30.58; N, 7.71; S, 17.32.

EXAMPLE 8

Bis(1,1-dimethylethyl) N,N'-[thiobis[(methyl)-imino)carbonyloxy]]bis[2,2,2-trifluoroethanimidothioate]

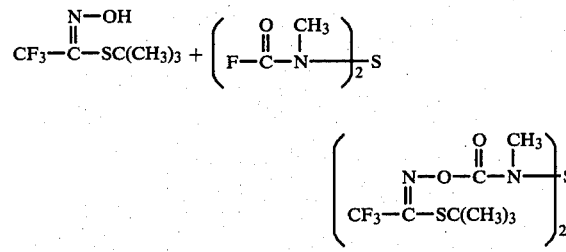

Triethylamine, 6.12 ml (0.04 mol), was added dropwise to a solution of 8.05 g (0.04 mol) of S-(1,1-dimethylethyl) (Z)-2,2,2-trifluoro-N-hydroxythioacetimidate and 3.68 g (0.02 mol) of N,N'-thiobis[N-methylcarbamoyl fluoride] in 50 ml of tetrahydrofuran. The reaction mixture was stirred for 2.5 hours, evaporated to dryness, and then taken up in CH$_2$Cl$_2$, washed with water, dried (MgSO$_4$), and evaporated again. There was obtained 8.0 g of bis(1,1-dimethylethyl) N,N'-[thiobis[(methylimino)-carbonyloxy]]bis[2,2,2-trifluoroethanimidothioate] as a viscous syrup: n$_D^{25}$ 1.473.

The S-(1,1-dimethylethyl) (Z)-2,2,2-trifluoro-N-hydroxythioacetimidate used above was prepared as follows:

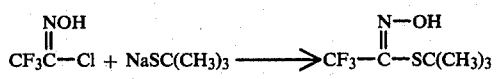

2-Methyl-2-propanethiol, 18.04 g (0.2 mol), was added dropwise to a solution prepared by dissolving 4.14 g (0.18 mol) of sodium in 60 ml of methanol. The reaction mixture was cooled to 0°, and 26.55 g (0.18 mol) of trifluoroacetohydroxamoyl chloride was added dropwise. The reaction mixture was allowed to warm to 25° and stirred for 18 hours, filtered to remove NaCl, and then distilled to give 29.19 g (81%) of S-(1,1-dimethylethyl) (Z)-2,2,2-trifluoro-N-hydroxythioacetimidate as a colorless liquid: bp 55° (1.7 mm); $^{19}$F NMR (CDCl$_3$) δ−67.6 ppm (s); $^1$H NMR δ1.51 ppm (s, 9H) and 9.70 ppm (OH).

Anal. Calcd. for C$_6$H$_{10}$F$_3$NOS: C, 35.81; H, 5.01; F, 28.33; N, 6.96; S, 15.94. Found: C, 35.80; H, 5.16; F, 28.23; N, 6.65; S, 15.87.

EXAMPLE 9

Diphenyl N,N'-[thiobis[(methylimino)carbonyloxy]]-bis[2,2,2-trifluoroethanimidothioate], Z,Z-isomer

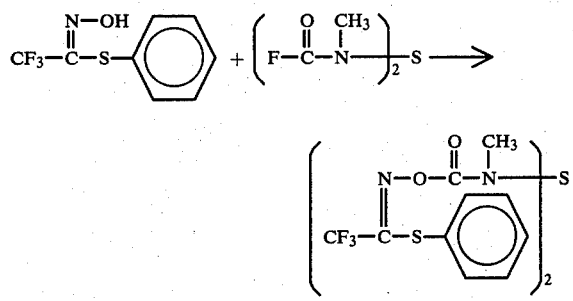

Triethylamine, 4.05 g (0.04 mol), was added dropwise at 0° to a solution of 3.69 g (0.02 mol) of N,N'-thiobis[N-methylcarbamoyl fluoride] and 8.85 g (0.02 mol) of S-phenyl (Z)-2,2,2-trifluoro-N-hydroxythioacetimidate in 50 ml of tetrahydrofuran. The reaction mixture was stirred for 2 hours at 25°, and then evaporated to dryness. The residue was broken up, washed with water, and then recrystallized from heptane to give 9.19 g (78%) of diphenyl N,N'-[thiobis[(methylimino)carbonyloxy]]bis-[2,2,2-trifluoroethanimidothioate] as colorless crystals; mp 98°–100°; ir (KBr) 5.65μ (C=O), 6.38μ (C=N); $^{19}$F NMR (CDCl$_3$) δ−62.4 ppm (s); $^1$H NMR (CDCl$_3$)δ3.55 ppm (s, 3H) and 7.3–7.9 ppm (m, 5H).

Anal. Calcd. for C$_{20}$H$_{16}$F$_6$N$_4$O$_4$S$_3$: C, 40.95; H, 2.75; N, 9.55. Found: C, 40.88; H, 2.80; N, 9.57.

The S-phenyl (Z)-2,2,2-trifluoro-N-hydroxythioacetimidate was prepared as follows:

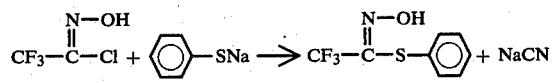

Thiophenol, 11.02 g (0.1 mol), was added dropwise to a solution prepared by dissolving 2.3 g (0.1 mol) of sodium in 50 ml methanol. The reaction mixture was cooled to 0°, and 14.75 (0.1 mol) of trifluoroacetohydroxamoyl chloride was added dropwise. The reaction mixture was warmed to 25°, stirred for 18 hours, and then filtered. The filtrate was evaporated to dryness, and the residue was recrystallized from hexane to give 16.3 g (74%) of S-phenyl (Z)-2,2,2-trifluoro-N-hydroxythioacetimidate as colorless crystals; mp 64°-66°; ir (KBr) 3.07μ (OH) and 6.23μ (C=N); $^{19}$F NMR (CDCl$_3$) δ−63.9 ppm (s); $^1$H NMR (CDCl$_3$) δ7.2-7.8 ppm (m, 5H) and 9.9 ppm (OH).

Anal. Calcd. for C$_8$H$_6$F$_3$NOS: C, 43.43; H. 2.73; N, 6.33 Found: C, 43.04; H, 2.82; N, 6.12.

EXAMPLE 10

Di(2-propenyl) N,N'-[thiobis[(methylimino)carbonyloxy]]bis[2,2,2-trifluoroethanimidothioate], Z,Z-isomer

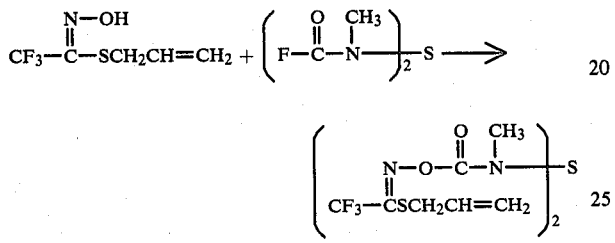

Triethylamine, 2.03 g (0.02 mol), was added dropwise to a solution of 3.7 g (0.02 mol) of S-(2-propenyl) (Z)-2,2,2-trifluoro-N-hydroxythioacetimidate and 1.85 g (0.01 mol) of N,N'-thiobis[N-methylcarbamoyl fluoride] in 25 ml of tetrahydrofuran cooled to 0°. The reaction mixture was stirred for 2 hours at 25° and then evaporated to dryness under reduced pressure. The residue was broken up, washed with water, and recrystallized from heptane to give 2.70 g (53%) of di(2-prophenyl)N,N'[thiobis[(methylimino)carbonyloxy]]-bis[2,2,2-trifluoroethanimidothioate], Z,Z-isomer, as colorless crystals: mp 103°-105°; $^{19}$F NMR (CDCl$_3$) δ−64.0 ppm (s); $^1$H NMR (CDCl$_3$) δ3.56 ppm (s, 3H), 3.87 ppm (d, J=6 Hz, 2H) and 5.1-6.2 ppm (m, 3H).

Anal. Calcd. for C$_{14}$H$_{16}$F$_6$N$_4$O$_4$S$_3$: C, 32.68; H, 3.14; N, 10.89. Found: C, 32.89; H, 3.18; N, 11.00.

The S-(2-propenyl) (Z)-2,2,2-trifluoro-N-hydroxythioacetimidate used above was prepared as follows:

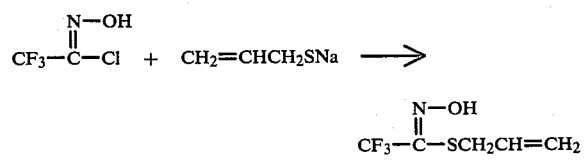

Allylmercaptan, 13 ml of 70% purity (0.11 mole), was added dropwise to a solution prepared by dissolving 2.3 g (0.1 mol) of sodium in 50 ml of methanol. The reaction mixture was cooled to 0°, and 14.75 g (0.1 mol) of trifluoroacetohydroxyamoyl chloride was added dropwise. The reaction mixture was stirred at 25° for 18 hours, and then filtered to remove NaCl. The filtrate was distilled to give 7.5 g of a colorless oil, bp 62°-68° (1.6 mm). On standing, gel-like particles developed that were removed by centrifugation to give 6.8 g of S-(2-propenyl) (Z)-2,2,2-trifluoro-N-hydroxythioacetimidate as the supernatant liquid $^{19}$F NMR (CDCl$_3$) δ−66.5 ppm (s); $^1$H NMR (CDCl$_3$) δ2.91 ppm (d, J=5 Hz, 3H), 3.13 ppm (s, 6H) and 6.57 ppm (NH).

Anal. Calcd. for C$_5$H$_{10}$F$_3$N$_3$O$_2$: C, 32.43; H, 3.27; N, 7.57. Found: C, 32.32; H, 3.37; N, 7.77.

EXAMPLE 11

N-[N-[N-(1-(Methylthio)ethylidineaminooxycarbonyl)-N-methylaminothio]-N-methylaminocarbonyloxy]-2,2,2-trifluoroethaneimidothioic Acid, Methyl Ester

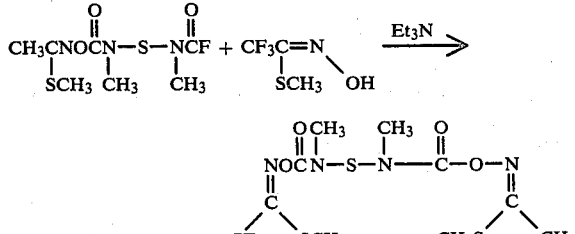

A solution of 1.47 g (10 mmol) of methyl (Z)-2,2,2-trifluoro-N-hydroxyethaneimidothioate and 2.63 g (9.8 mmol) of N-[N-[N-methyl-N-(fluorocarbonyl)-aminothio]-N-methylaminocarbonyloxy]ethaneimidothioic acid methyl ester in 25 ml of tetrahydrofuran was treated dropwise with 1.11 g (1.53 ml, 11 mmol) of triethylamine and allowed to stir at room temperature for 18 hours. The solvent was evaporated at reduced pressure to give a white powder. This solid was then dissolved in 20 ml of methylene chloride and washed with 20 ml of water. The organic phase was separated, dried over magnesium sulfate and evaporated to dryness at reduced pressure to give 3.02 g (75%) of the crude product as a white powder. Recrystallization from 27 ml of chlorobutane gave 2.43 g (61%) of methyl N-[N-[N-(1-(methylthio)-ethylidineaminooxycarbonyl)-N-methylamino]-N-methylaminocarbonyloxy]-2,2,2-trifluoroethaneimidothioate as colorless crystals; mp 111°-112°; $^1$H NMR (CDCl$_3$) δ3.53 ppm (s, N-CH$_3$); δ3.53 ppm (s, N-CH$_3$); δ3.50 (s, N-CH$_3$); δ2.62 (q, J≈1.5 Hz, SCH$_3$ on C-CF$_3$); δ2.42 (s, S-CH$_3$ on C-CH$_3$); δ2.32 (s, C-CH$_3$). $^{19}$F NMR (CDCl$_3$) δ−63.74 ppm (q, J$_{F,H}$=15 Hz).

Anal. Calcd. for C$_{10}$H$_{15}$N$_4$O$_4$S$_3$F$_3$: C, 29.40; H, 3.70; N, 13.72. Found: C, 29.26; H, 3.69, N, 13.54.

EXAMPLE 12

N-[N-[N-(1-methylthio)ethylidineaminooxycarbonyl)-N-methylaminothio]-N-methylaminocarbonyloxy]-2,2,2-trifluoroethaneimidothioic Acid, Ethyl Ester

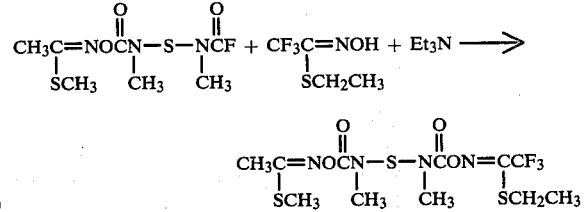

A solution of 0.94 g (3.5 mmol) of N-[N-[N-methyl-N-(fluorocarbonyl)aminothio]-N-methylaminocarbonyloxy]ethaneimidothioic acid, methyl ester, and 0.54 g (3.33 mmol) of ethyl (Z)-2,2,2-trifluoro-N-hydroxyethaneimidothioate in 10 ml of THF was treated dropwise with 0.5 ml (3.6 mmol) of triethylamine. The solution was stirred for 1 hour, the solvent was evaporated at reduced pressure, and the residual oil was taken up in $CH_2Cl_2$, washed with water, dried and evaporated to give a viscous material that crystallized on standing to an off-white solid. The product, 0.80 g (60%), was recrystallized from 20 ml of heptane to give ethyl N-[N-[N-(1-(methylthio)ethylidineaminooxycarbonyl)-N-methylaminocarbonyl)-N-methylaminothio]-N-methylaminocarbonyloxy]-2,2,2-trifluoroethaneimidothioate as a white crystalline solid: 0.52 g (40%); mp 97°–98°; $^1H$ NMR ($CDCl_3$) δ1.37 ppm (t, 3H); δ2.32 (s, 3H, $CCH_3$); δ2.43 (s, 3H, $SCH_3$); δ2.43 (s, 3H, $SCH_3$); δ3.22 (q, 2H); δ3.5 (s) and δ3.53 (s) together 6H, $SNCH_3$'s. $^{19}F$ NMR ($CDCl_3$) δ−64.06 ppm.

Anal. Calcd. for $C_{11}H_{17}F_3N_4O_4S_3$: C, 31.27; H, 4.06; N, 13.26. Found: C, 31.56; H, 4.13; N, 13.33.

EXAMPLE 13

N-[N-[N-[2-(dimethylamino)-1-methylthio-2-oxoethylidineaminooxycarbonyl]-N-methylaminodithio]-N-methylaminocarbonyloxy]-2,2,2-trifluoroethaneimidothioic Acid, Methyl Ester

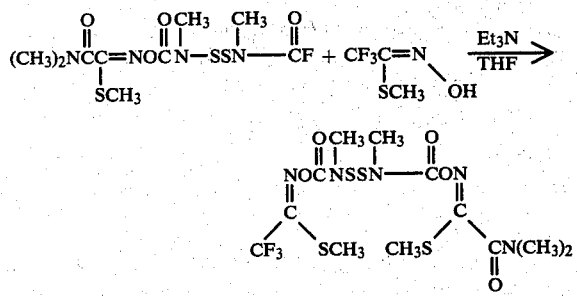

A fine suspension of 3.76 g (10.5 mmol) of methyl N-[N-[N-methyl-N-(fluorocarbonyl)aminodithio]-N-methylaminocarbonyloxy]-2-(dimethylamino)-2-oxoethaneimidothioate and 1.47 g (10 mmol) of S-methyl (Z)-2,2,2-trifluoro-N-hydroxyethaneimidothioate in 50 ml of THF was treated dropwise with 1.11 g (11 mmol, 1.53 ml) of triethylamine and stirred for 18 hours. At the end of this period, most of the solids were in solution. The solution was evaporated to dryness to give a pale yellow residue. Chlorobutane was added to the residue and undissolved crystals of a by-product were filtered off. The filtrate was evaporated to dryness to give 3.42 g of methyl N-[N-[N-[2-(dimethylamino)-1-methylthio-2-oxoethylidineaminooxycarbonyl]-N-methylaminodithio]-N-methylaminocarbonyloxy]-2,2,2-trifluoroethaneimidothioate as a pale yellow transparent gum: $^1H$ NMR ($CDCl_3$) δ2.34 ppm (s, 3H), 2.70 ppm (q, J=1.5 Hz, 3H), 3.05 ppm (s, 3H), 3.12 ppm (s, 3H), 3.40 ppm (s, 3H) and 3.40 ppm (s, 3H).

Anal. Calcd. m/e for $C_{12}H_{18}F_3N_5O_5S_4$: 278.9743. Measured m/e: 278.9531.

EXAMPLE 14

N-N-[N-(2-Dimethylamino)-1(methylthio)-2-oxyethylidineaminooxycarbonyl]-N-methylaminothio]-N-methylaminocarbonyloxy]-2,2,2-trifluoroethaneimidothioic Acid, Methyl Ester

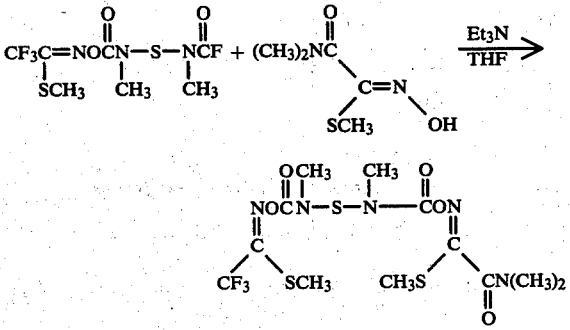

A solution of 0.15 g (0.5 mmol) of methyl N-[N-[N-methyl-N-(fluorocarbonyl)aminothio]-N-methylaminocarbonyloxy]-2,2,2-trifluoroethaneimidothioate and 0.08 g of methyl 2-(N-dimethylaminocarbonyloxy)-N-hydroxymethaneimidothioic acid in 2 ml of tetrahydrofuran was treated dropwise with 0.076 ml of triethylamine and allowed to sit overnight. The THF was evaporated and the residue was dissolved in methylene chloride, washed with water, dried and evaporated to dryness to give 0.23 g of methyl N-[N-[N-(2-dimethylamino)-1-(methylthio)-2-oxoethylidineaminooxycarbonyl]-N-methylaminothio]-N-methylaminocarbonyloxy]-2,2,2-trifluoroethaneimidothioate as a colorless glass; $^{19}F$ NMR ($CDCl_3$) δ−63.74 ppm (q).

EXAMPLE 15

Propyl 2-(Dimethylamino)-N-[N-methyl-N-[N-methyl N-[[2,2,2-trifluoro-1-(propylthio)ethylidene]aminooxycarbonyl]aminothio]aminocarbonyloxy]-2-oxoethanimidothioate

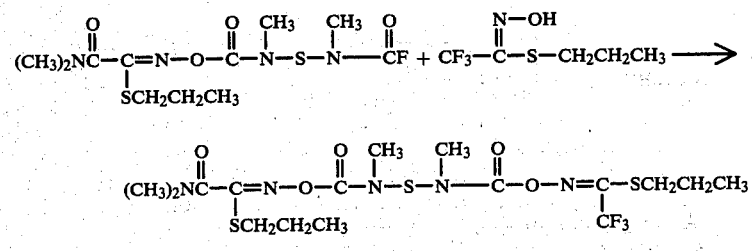

Triethylamine, 1.53 ml (0.008 mol), was added to a solution of 2.90 g (0.008 mol) of propyl 2-(dimethylamino)-N-[N-[N-methyl-N-(fluorocarbonyl)-aminothio]-N-methylaminocarbonyloxy]-2-oxoethaneimidothioate and 1.49 g (0.008 mol) S-propyl (Z)-N-hydroxythioacetimidate in 10 ml tetrahydrofuran, and the reaction mixture was stirred for 24 hours, and then evaporated to dryness. The residue was taken up in $CH_2Cl_2$, washed with water, dried ($MgSO_4$), and evaporated to give a honey-colored oil. Preparative higher pressure liquid chromatography gave 1.4 g of the product as a colorless oil: $^{19}F$ NMR ($CDCl_3$) δ−63.94 ppm (s).

EXAMPLE 16

Dimethyl
N,N'-[2,3-butanediylidenebis[nitrilooxycarbonyl-(N-methylimino)thio-(N-methylimino)carbonyloxy]]bis-[2,2,2-trifluoroethaneimidothioate]

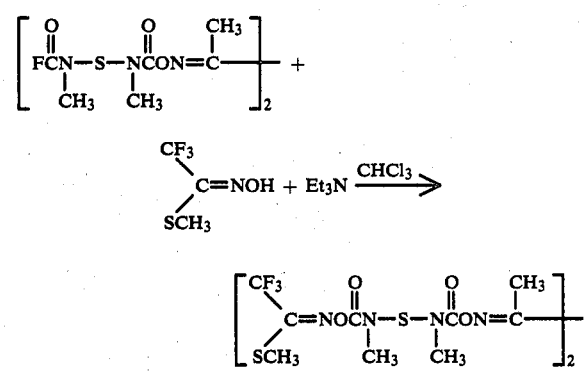

A mixture of 2.22 g (5 mmol) of the above difluoride suspended in 50 ml of chloroform and 1.47 g (10 mmol) of S-methyl (Z)-2,2,2-trifluoro-N-hydroxyethaneimidothioate was treated dropwise with 1.53 ml (1.11 g, 0.011 mmol) of triethylamine and then stirred for 20 minutes. The solvent was evaporated, the beige powdery residue was taken up in $CH_2Cl_2$, washed with water, extracted, dried and evaporated to dryness to give a light beige powder. Recrystallization from 30 ml of chlorobutane gave the product as a white powder mp 167°-169°, 1.89 g (crop 1)+0.29 g (crop 2), mp. 160°-162°. $^1$H NMR ($CDCl_3$) δ2.38 (s, 6H, C-$CH_3$'s); δ2.63 (q, 6H, S-$CH_3$'s); δ2.61 (s) and δ2.65 (s) [together 12H, N-$CH_3$'s]. $^{19}$F NMR ($CDCl_3$) δ−63.72, $CF_3$ coupled to $SCH_3$.

Anal. Calcd. for $C_{18}H_{24}F_6N_8O_8S_4$: C, 29.91; H, 3.35; N, 15.50. Found: C, 31.30; H, 3.58; N, 15.32.

Intermediates useful for the preparation of new compounds of this invention such as by Examples 11 to 16 include:

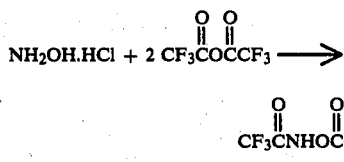

A 928 g (4.4 mol) sample of trifluoroacetic anhydride was added dropwise to 140 g (2 mol) of powdered hydroxylamine hydrochloride at such a rate that the evolution of hydrogen chloride did not become too vigorous. A reflux condenser cooled to −78° with solid carbon dioxide-acetone was used to prevent the evolved HCl from carrying out unreacted trifluoroacetic anhydride. The reaction mixture was stirred overnight and then evaporated to dryness under reduced pressure. The white residue was broken up and dried in a vacuum desiccator over $P_2O_5$ to give 373.73 g (83%) of crude N,O-bis(trifluoroacetyl)hydroxylamine. A similar sample recrystallized from methylene chloride was obtained as colorless crystals: mp 40°-50°; ir (Nujol) 5.41 and 5.86μ; $^{19}$F NMR (ether) δ−73.7 ppm (s) and −74.5 ppm (s).

Anal. Calcd. for $C_4HF_6NO_3$: C, 21.35; H, 0.44; F, 50.56; N, 6.22. Found: C, 21.38; H, 0.87; F, 50.81; N, 6.76.

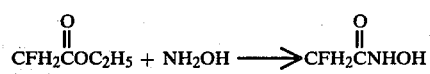

A solution of 1 mol of sodium methoxide in 600 ml methanol was added dropwise to a stirred suspension of 69.5 g (1 mol) of hydroxylamine hydrochloride in 200 ml of methanol containing 0.02 g phenolphthalein. A small additional quantity of $NH_2OH.HCl$ was added to discharge the pink color. The precipitated NaCl was filtered off and then 106.1 g (1 mol) of ethyl fluoroacetate was added dropwise to the filtrate. The reaction mixture was stirred for 5 days at 25°, and then evaporated to dryness under reduced pressure to give 90.28 g (97%) of crude product. Recrystallization from isopropanol gave 52.4 g (56%) of 2-fluorohydroxamic acid as colorless, hydroscopic crystals: mp 92°-94°; $^1$H NMR (DMSO-$d_6$) δ4.83 ppm (d, J=47 Hz, 2H) and 9.87 ppm (broad, 2H); $^{19}$F NMR (DMSO-$d_6$) δ−229.4 ppm (t, J=47 Hz, 90%) and −236.5 ppm (t, J=47 Hz, 10%).

Anal. Calcd. for $C_2H_4FNO_2$: C, 25.81; H, 4.33; F, 20.42; N, 15.05. Found: C, 26.15; H, 4.55; F, 20.57; N, 15.32.

N-(fluoroacetyl)-O-(trifluoroacetyl)hydroxylamine

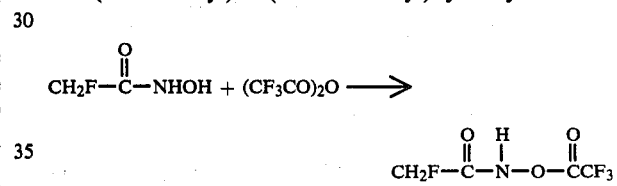

Trifluoroacetic anhydride, 71 ml (0.5 mol), was added dropwise to a 37.22 g (0.4 mol) sample of powdered 2-fluoroacetohydroxamic acid. The reaction mixture became liquid and warmed spontaneously to 60°. After cooling, the reaction mixture was evaporated to dryness under reduced pressure to give 70.3 g (93%) of N-(fluoroacetyl)-O-(trifluoroacetyl)-hydroxylamine as a colorless, crystalline residue: mp 56°-59°; $^1$H NMR ($CDCl_3$) δ5.05 ppm (d, J=47 Hz, 2H) and 9.8 ppm (NH); $^{19}$F NMR ($CDCl_3$) δ−233.8 ppm (t, J=47 Hz, 1F) and 73.8 ppm (s, 3F).

Anal. Calcd. for $C_4H_3F_3NO_3$: C 25.41; H, 1.60; F, 40.20; N, 7.41. Found: C, 25.01; H, 2.00; F, 40.59; N, 7.18.

2-Fluoro-O-(trifluoroacetyl)acetohydroxamoyl Chloride

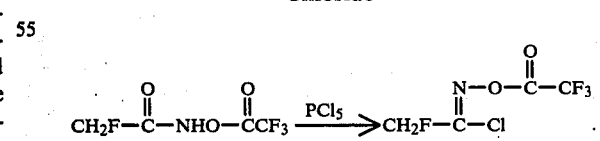

A mixture of 66.2 g (0.35 mol), of crude N-(fluoroacetyl)-O-(trifluoroacetyl)hydroxyamine and 94 g (0.45 mol) of phosphorus pentachloride was heated in a simple still. The distillate below 130° was redistilled through a spinning band still to give 60.42 g of phosphorus oxychloride, bp 100°-108°, and 35.33 g (49%) of 2-fluoro-O-(trifluoroacetyl)-acetohydroxyamoyl chloride as a colorless liquid: bp 126°-127°; $^{19}$F NMR (CCl$_3$F) δ −74.2 ppm (s, 3F) and −223.3 ppm (t, J=46 Hz, 1F); $^1$H NMR (CCl$_3$F) δ5.15 ppm (d, J=46 Hz); ir (liquid) 5.47μ (C=O) and 6.16δ (C=N).

Anal. Calcd. for C$_4$H$_2$ClF$_4$NO$_2$: C, 23.15; H, 0.97; F, 36.62; N, 6.75. Found: C, 22.95, H, 1.11; F, 37.01; N, 6.69.

TABLE I $$\underset{R^2S}{\overset{XYFC}{\diagdown}}C=NO\overset{O}{\overset{\|}{C}}\underset{CH_3}{\overset{|}{N}}-S_n(O)_m-\underset{CH_3}{\overset{|}{N}}\overset{O}{\overset{\|}{C}}OR^1$$

| X | Y | n | m | R² | R¹ |
|---|---|---|---|----|----|
| F | F | 1 | 0 | CH₃ | −N=C(CF₃)(SCH₃) |
| H | F | 1 | 0 | CH₃ | −N=C(CF₂H)(SCH₃) |
| H | H | 1 | 0 | CH₃ | −N=C(CFH₂)(SCH₃) |
| F | F | 1 | 0 | CH₃ | −N=C(CH₃)(SCH₃) |
| H | F | 1 | 0 | CH₃ | −N=C(CH₃)(SCH₃) |
| H | H | 1 | 0 | CH₃ | −N=C(CH₃)(SCH₃) |
| F | F | 1 | 0 | CH₃ | −N=C(CON(CH₃)₂)(SCH₃) |
| H | F | 1 | 0 | CH₃ | −N=C(CON(CH₃)₂)(SCH₃) |
| H | H | 1 | 0 | CH₃ | −N=C(CON(CH₃)₂)(SCH₃) |
| F | F | 1 | 0 | CH₃ | −N=CHC(CH₃)(SCH₃)(CH₃) |
| H | F | 1 | 0 | CH₃ | −N=CHC(CH₃)(SCH₃)(CH₃) |
| H | H | 1 | 0 | CH₃ | −N=CHC(CH₃)(SCH₃)(CH₃) |
| F | F | 1 | 0 | CH₃ | 2,2-dimethyl-2,3-dihydrobenzofuran-7-yl (8-methyl) |
| H | F | 1 | 0 | CH₃ | 2,2-dimethyl-2,3-dihydrobenzofuran-7-yl (8-methyl) |
| H | H | 1 | 0 | CH₃ | 2,2-dimethyl-2,3-dihydrobenzofuran-7-yl (8-methyl) |
| F | F | 1 | 0 | CH₃− | −N=C(CH₂OCH₃)(SCH₃) |
| F | F | 1 | 0 | CH₃− | −N=C(CH₂CH₃)(SCH₃) |
| F | F | 1 | 0 | CH₃CH₂− | −N=C(CF₃)(SCH₂CH₃) |
| F | F | 1 | 0 | CH₃CH₂− | −N=C(CH₃)(SCH₃) |
| F | F | 1 | 0 | CH₃− | −N=C(CH(CH₃)₂)(SCH₃) |
| F | F | 1 | 0 | (CH₃)₂CH− | −N=C(CF₃)(SCH(CH₃)₂) |
| F | F | 1 | 0 | CH₃CH₂CH₂− | −N=C(CF₃)(SCH₂CH₂CH₃) |
| F | F | 2 | 0 | CH₃ | −N=C(CF₃)(SCH₃) |
| F | F | 2 | 0 | CH₃ | −N=C(CH₃)(SCH₃) |

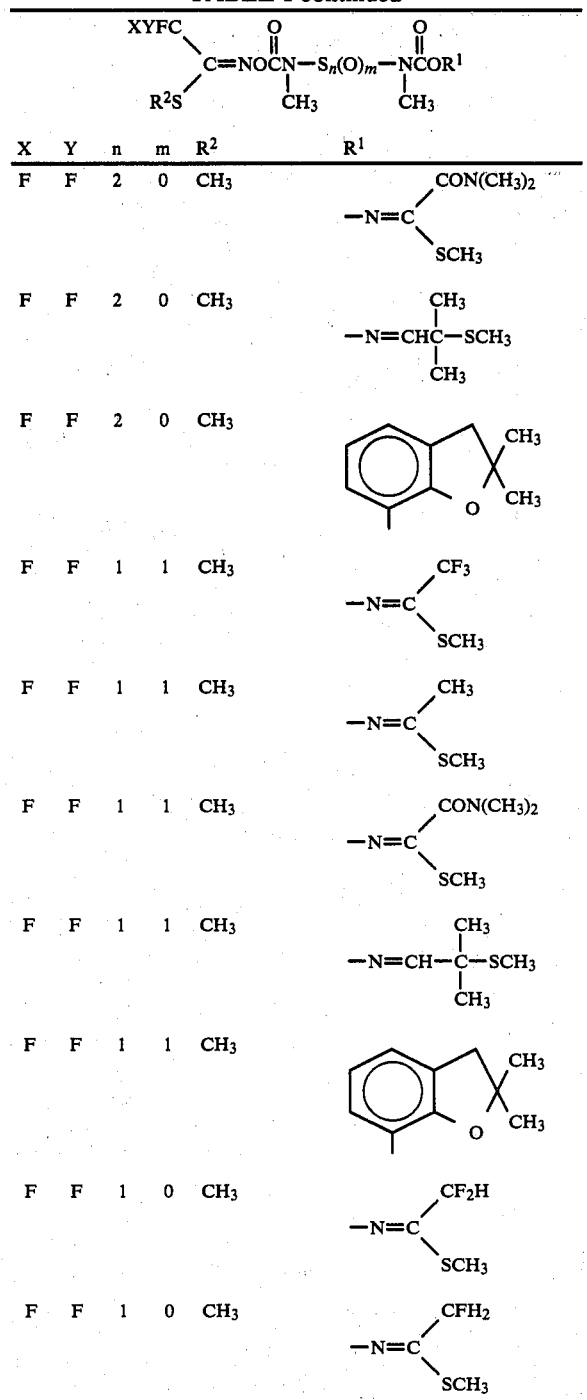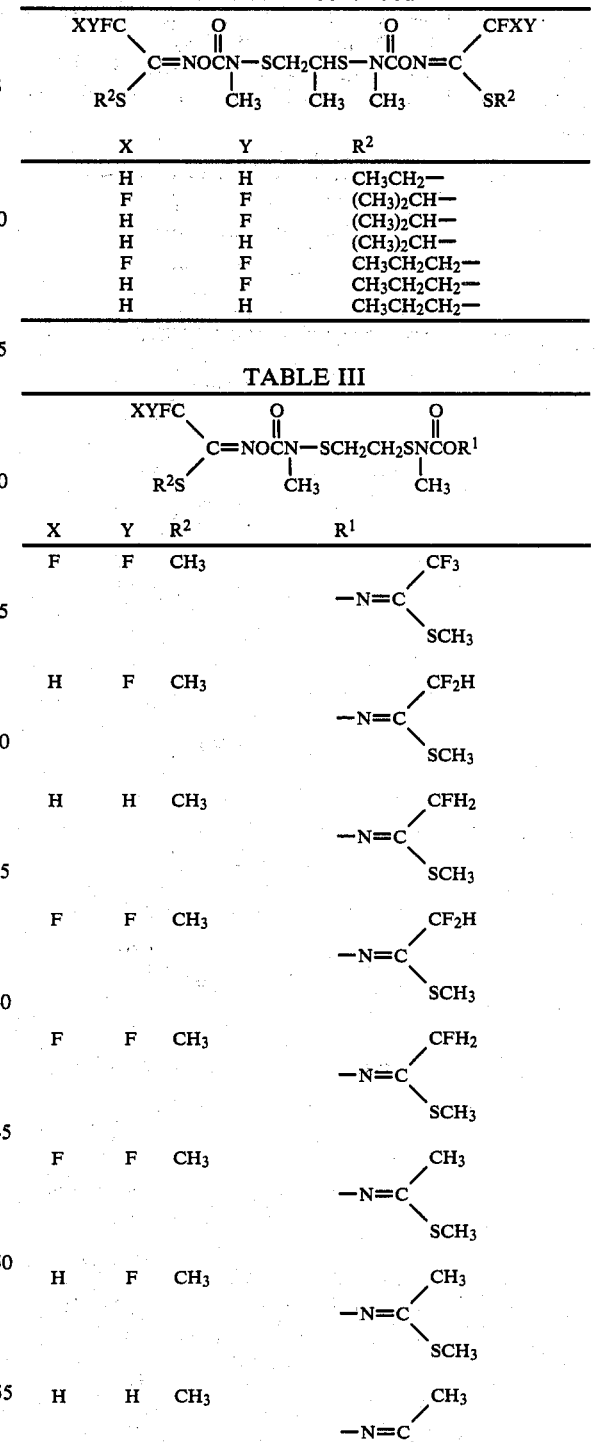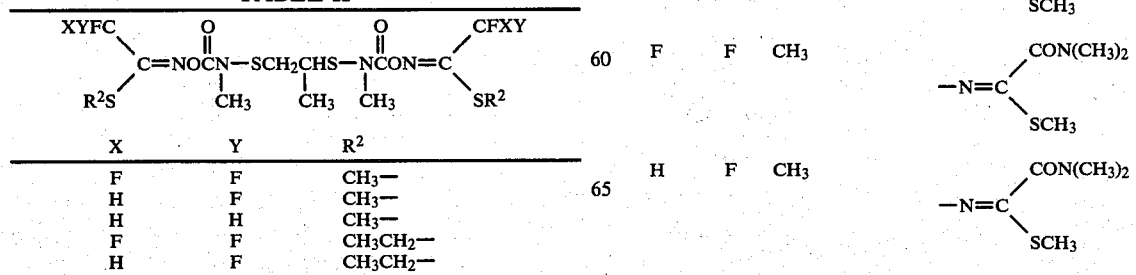

TABLE III-continued $$\underset{R^2S}{\overset{XYFC}{\diagdown}}C=NOC\underset{CH_3}{\overset{O}{\overset{\|}{N}}}-SCH_2CH_2S\underset{CH_3}{\overset{O}{\overset{\|}{N}}}COR^1$$

| X | Y | R² | R¹ |
|---|---|---|---|
| H | H | CH₃ | $-N=C\begin{smallmatrix}CON(CH_3)_2\\SCH_3\end{smallmatrix}$ |
| F | F | CH₃ | $-N=CHC(CH_3)(SCH_3)(CH_3)$ |
| H | F | CH₃ | $-N=CHC(CH_3)(SCH_3)(CH_3)$ |
| H | H | CH₃ | $-N=CHC(CH_3)(SCH_3)(CH_3)$ |
| F | F | CH₃ | (benzofuran-CH₃,CH₃) |
| H | F | CH₃ | (benzofuran-CH₃,CH₃) |
| H | H | CH₃ | (benzofuran-CH₃,CH₃) |
| F | F | CH₃CH₂— | $-N=C\begin{smallmatrix}CF_3\\SCH_2CH_3\end{smallmatrix}$ |
| F | F | (CH₃)₂CH | $-N=C\begin{smallmatrix}CF_3\\SCH(CH_3)_2\end{smallmatrix}$ |
| F | F | CH₃CH₂CH₂— | $-N=C\begin{smallmatrix}CF_3\\SCH_2CH_2CH_3\end{smallmatrix}$ |
| F | F | CH₃CH₂— | $-N=C\begin{smallmatrix}CH_3\\SCH_3\end{smallmatrix}$ |

Formulation

Useful formulations of the compounds of Formulae Ia and Ib can be prepared in conventional ways. They include dusts, granules, pellets, solutions, suspensions, emulsions, wettable powders, emulsifiable concentrates and the like. Many of these may be applied directly to the plant. Sprayable formulations can be extended in suitable media and used at spray volumes of from a few pints to several hundred gallons per acre. High strength compositions are primarily used as intermediates for further formulations. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

|  | Active Ingredient | Diluent(s) | Surfactant(s) |
|---|---|---|---|
| Wettable Powders | 20-90 | 0-74 | 1-10 |
| Oil Suspensions, Emulsions, Solutions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. McCutcheon's "Detergents and Emulsifiers Annual", MC Publishing Co., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions can be prepared by simply mixing the ingredients. Fine solid compositions can be made by blending and, usually, grinding as in a hammer or fluid energy mill. Suspensions can be prepared by wet milling. Granules and pellets may be made by spraying the active material upon preformed granular carriers or by known agglomeration techniques.

EXAMPLE A

Wettable Powder

N,N-[thiobis[(methylimino)carbonyloxy]]bis[2,2,2-trifluoroethanimidothioic acid] dimethyl ester: 30%
Dioctyl sodium sulfosuccinate: 1.5%
Sodium ligninsulfonate: 3%
Low viscosity methyl cellulose: 1.5%
Attapulgite: 64%

The ingredients are thoroughly blended, passed through an air mill to produce an average particle size under 15 microns, reblended, and sifted through a U.S.S. No. 50 sieve (0.3 mm openings) before packaging.

All compounds of this invention may be formulated in the same manner.

EXAMPLE B

Wettable Powder

N-[N-[N-(1-(methylthio)ethylideneaminooxycarbonyl)-N-methylaminothio]-N-methylaminocarbonyloxy]-2,2,2-trifluoroethanimidothioic acid, methyl ester: 50%
Sodium alkylnaphthalenesulfonate: 2%
Low viscosity methyl cellulose: 2%
Diatomaceous earth: 46%

The ingredients are blended, coarsely hammermilled and then air milled to produce particles of active ingredients practically all below about 10 microns in diameter. The product is reblended before packaging.

EXAMPLE C

Dust

Wettable powder of Example B: 10%
Pyrophyllite (powder): 90%

The wettable powder and the pyrophyllite diluent are thoroughly blended and then packaged. The product is suitable for use as a dust.

EXAMPLE D

Solution

N-[N-[N-(1-methylthio)ethylideneaminooxycarbonyl)-N-methylaminothio]-N-methylaminocarbonyloxy]-2,2,2-trifluoroethanimidothioic acid, methyl ester: 30%
Dimethylformamide: 70%

The ingredients are combined and stirred to produce a solution, which can be used for low volume applications.

EXAMPLE E

Emulsifiable Concentrate

N,N'-[thiobis[(methylimino)carbonyloxy]]bis[2,2,2-trifluoroethanimidothioic acid], dimethyl ester: 20%
Blend of oil soluble sulfonates and polyoxyethylene esters: 4%
Xylene: 76%

The ingredients are combined and stirred with gentle warming to speed solution. A fine screen filter is included in the packaging operation to insure the absence of any extraneous undissolved material in the product.

EXAMPLE F

Granule

Wettable powder of Example A: 15%
Gypsum: 69%
Potassium sulfate: 16%

The ingredients are blended in a rotating mixer and water sprayed on to accomplish granulation. When most of the material has reached the desired range of 1.0 to 0.42 mm (U.S.S. No. 18 to 40 sieves), the granules are removed, dried and screened. Oversize material is crushed to produce additional material in the desired range. These granules contain 4.5% active ingredient.

EXAMPLE G

Aqueous Suspension

N-[N-[N-(1-methylthio)ethylideneaminooxycarbonyl)-N-methylaminothio]-N-methylaminocarbonyloxy]-2,2,2-trifluoroethanimidothioic acid, methyl ester: 25%
Hydrated attapulgite: 3%
Crude calcium ligninsulfonate: 10%
Sodium dihydrogen phosphate: 0.5%
Water: 61.5%

The ingredients are ground together in a ball or roller mill until the solid particles have been reduced to diameters under 10 microns.

Use

The compounds of Formulae Ia and Ib have insecticidal activity on major agricultural, public health and household pests. For reasons of activity, the compounds of Formula I are preferred.

The examples demonstrate the control efficacy of these compounds.

These compounds have a wide spectrum of insecticidal activity, controlling economically significant pest species in the orders Lepidoptera, Homoptera, Diptera and Coleoptera. More specifically, insects controlled by these compounds include, but are not limited to; the southern armyworm (*Spodoptera eridania*), beet armyworm (*Spodoptera exigua*), bean aphid (*Aphis fabae*), housefly (*Musca domestica*), boll weevil (*Anthonomus grandis*), tobacco budworm (*Heliothis Virescens*), corn rootworm (*Diabrotica spp.*), and corn wireworm (*Melanotus cribulosus*).

Control is achieved through application of one or more of the compounds of Formulae Ia and Ib to the area to be protected, to the pests themselves, and/or the locus of infestation. The usual methods of application to agricultural crops, using compounds of this invention, are by foliar applications, soil applications, or applications to those plant parts which are to be protected. Applications, however, are not limited to these methods. The rate of application required for effective control is dependent upon both biological factors, e.g., the pest species, its life stage, size, and location, and upon nonbiological factors, e.g., weather conditions (temperature, rainfall, humidity, etc.), time of year, application method, crop (plant growth habit and characteristics), and agronomic factors (crop spacing, soil type, etc.). In general, application rates of 0.07 to 8 kg/ha may be required for pest control in agriculture, the rates being dependent upon the above listed biological and non-biological factors. However, rates of 0.14 to 2 kg/ha will, under normal circumstances result in effective control. Rates of 0.28 to 1.5 kg/ha will normally be used in large scale field operations.

Compounds of Formulae Ia and Ib can be mixed with insecticides, fungicides, nematicides, bactericides, acaricides, and/or other biologically active compounds, in order to achieve effective control with a minimum of input of material, time, and effort. The mixture ratio for each part by weight of compounds of this invention with the above listed biologically active chemicals may vary from 0.20 to 5.00 parts by weight. The following list consists of a few select examples of chemicals presently employed in the above listed control classes. The mixture composition, however, is not to be construed as being limited solely to the various possible combinations of those compounds.

Insecticides 3-hydroxy-N-methylcrotonamide (dimethylphosphate)ester (Azodrin ®)
methylcarbamic acid, ester with 2,3-dihydro-2,2-dimethyl-7-benzofuranol (Furadan ®)
O-[2,4,5-trichloro-α-(chloromethyl)benzyl]phosphoric acid, O',O'-dimethyl ester (Gardona ®)
2-mercaptosuccinic acid, diethyl ester S-ester with thionophosphoric acid, dimethyl ester (Malathion ®)
phosphorothioic acid, O,O-dimethyl, O-p-nitrophenyl ester (methyl parathion)
methylcarbamic acid, ester with α-naphthol (Sevin ®)
methyl O-(methylcarbamoyl) thiolacetohydroxamate (methomyl)
N'-(4-chloro-o-tolyl)-N,N-dimethylformamidine (Galecron ®)
O,O-diethyl-O-(2-isopropyl-4-methyl-6-pyrimidylphosphorothioate (Diazinon ®)
octachlorocamphene (toxaphene)
O-ethyl O-p-nitrophenyl phenylphosphonothioate (EPN)
cyano(3-phenoxyphenyl)-methyl-4-chloro-α-(1-methylethyl)-benzeneacetate (Pydrin ®)
(3-phenoxyphenyl)methyl(±)-cis,trans-3-(2,2-dichloroethenyl)-2,2-dimethylcyclopropanecarboxylate (Ambush ®)
O-ethyl-S-(p-chlorophenyl)ethylphosphonodithioate (Curacron ®)
phosphorothithionic acid, O-ethyl-O-[4-(methylthio)-phenyl]-S-n-propyl ester (Bolstar ®)

Fungicides methyl 2-benzimidazolecarbamate (carbendazim)
tetramethyl thiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide Curzate ®
N-trichloromethylthiotetrahydrophthalimide (captan)
N-trichloromethylthiophthalimide (folpet)

Nematicides

S-methyl 1-(dimethylcarbamoyl)-N-(methylcarbamoyloxy)-thioformimidate
S-methyl 1-carbamoyl-N-(methylcarbamoyloxy)thioformimidate
N-isopropylphosphoramidic acid, O-ethyl-O'-[4-(methylthio)-m-tolyl]diester (Nemacur ®)

Bactericides tribasic copper sulfate
streptomycin sulfate

Acaricides senecioic acid, ester with 2-sec-butyl-4,6-dinitrophenol (Morocide ®)
6-methyl-1,3-dithiolo[2,3-β]quinonolin-2-one (Morestan ®)
ethyl 4,4'-dichlorobenzilate (Chlorobenzilate ®)
1,1-bis(p-chlorophenyl)-2,2,2-trichloroethane (Kelthane ®)
bis(pentochloro-2,4-cyclopentadien-1yl) (Pentac ®)
tricyclohexyl trihydroxide (Plictran ®)

EXAMPLE I

The foliage only of red kidney bean plants in the two-leaf stage was sprayed to run-off with dispersions of the compound named below at various concentrations. Dispersions were prepared by dissolving appropriately weighed quantities of the active ingredient in 10 ml of acetone and diluting to 100 ml with water containing a surface active agent (Duponol ® L-144 WDG) at 1:3000. After drying, leaves were excised and placed in covered 10 cm petri dishes along with moist filter paper to keep them fresh. Ten southern armyworm larvae were placed in each dish. Tests were run in duplicate. The units were kept in a room maintained at 25°±2° C., 53±5% RH. Results were recorded at the end of 2 days.

| Compound | % A.I. Spray Concentration | % Mortality (2 days) |
| --- | --- | --- |
| N,N'—[thiobis[(methylimino)carbonyloxy]]bis-[2,2,2-trifluoroethanimidothioic acid], | .005 | 100 |
| dimethyl ester | .002 | 100 |
| Untreated | — | 0 |

EXAMPLE II

The foliage of red kidney bean plants in the two-leaf stage was sprayed to run-off with dispersions of the compound named below at various concentrations. Dispersions were prepared by dissolving appropriately weighed quantities of the active ingredient in 10 ml of acetone and diluting to 100 ml with water containing a surface active agent (Duponol ® L-144 WDG) at 1:3000. After drying, plants were placed under artificial light in a room maintained at 25°±2° C., 54±5% RH. After the designated period, leaves were excised and placed in covered 10 cm petri dishes along with moist filter paper to keep them fresh. Ten southern armyworm larvae were placed in each dish. Tests were run in duplicate. The units kept in a room maintained at 25°±2° C., 54±5% RH. Results were recorded two days after larvae were placed on the treated foliage.

| Compound | % A.I. Spray Concentration | % Mortality (2 days) 2 days residual | 7 days residual |
| --- | --- | --- | --- |
| N,N'—[thiobis[(methylimino)carbonyloxy]]bis-[2,2,2-trifluoroethanimidothioic acid], | .01 | 100 | 100 |
| dimethyl ester | .005 | 100 | 100 |

EXAMPLE III

Potted Stoneville 213 cotton plants approximately 25 cm high having 3–4 true leaves were sprayed to run-off with aqueous dispersions of compounds of this invention at 500 ppm. The sprays contained a surface active agent (Duponol ® L-144 WDG) at a concentration of 1:3000. Another set of plants was similarly treated with methomyl. After drying, the plants were set out in the greenhouse and held for observation. Results were recorded after 6 days.

| Compound (500 ppm AI)[1] | Rating[2] (6 days) |
|---|---|
| N,N'—[thiobis[(methylimino)-carbonyloxy]]bis[2,2,2-trifluoroethanimidothioic acid], dimethyl ester | 0 |
| Methyl N—[[(methylamino)carbonyl]oxy]ethanimidothioate (methomyl) | 6R |
| Untreated control | 0 |

[1]AI — active ingredient
[2]"R" denotes typical methomyl effect, i.e., reddening of older leaves, slight puckering and black stippling of younger leaves. Rating is on the basis of 0 to 10 with 0 indicating no effect and 10 indicating total leaf area involvement.

EXAMPLE IV

Tobacco budworm, Heliothis virescens, larvae were treated topically with the compound named below. One microliter of each concentration used was applied to the dorso-prothoracic area of each larva tested. The stock solutions were prepared by dissolving appropriately weighed quantities of active ingredient in predetermined quantities of acetone. Further diluting with acetone yielded the desired concentrations. Larvae were treated in the individual 1-oz. cups in which they were reared on artificial diet. Fifteen larvae were treated with the desired concentration and kept in a growth room at 26°±0.5° C. and 50-60% RH. Mortality readings were taken at 72 hours.

| Compound | ug/larva | % Mortality |
|---|---|---|
| N,N'—[thiobis[(methylimino)-carbonyloxy]]bis[2,2,2-trifluoroethanimidothioic acid] dimethyl ester | 4 | 47 |

EXAMPLE V

Foliage disks (4 cm dia.) of Romaine lettuce were dip-treated with disperions of various concentrations of the compound named below. Dispersions were prepared by dissolving appropriately weighed quantities of the active ingredient in 10 ml of acetone and diluting to 100 ml with water containing surfactant F at 1:1000. Leaf disks were allowed to dry and then placed in 10 petri dishes along with water (1 ml) moistened filter paper. Five tobacco budworm larvae were placed in each dish. The units were kept at room temperature 2.6°±0.5° C., 50-60% RH. Mortality readings were taken at 48 hours.

| Compound | Concentration (ppm) | % Control |
|---|---|---|
| N,N'—[thiobis[(methylimino)-carbonyloxy]]bis[2,2,2-trifluoroethanimidothioic acid], dimethyl ester | 100 | 65 |
| | 50 | 47 |
| | 25 | 53 |

EXAMPLE VI

A grain of corn was placed on Michigan peat in each of a series of cups (2 inches×2 inches). The cups were sprayed with 250 ppm of the indicated compounds in acetone solution. The grains were then covered with more peat, and each cup was infested with 10 larvae of the southern corn rootworm. Percent rootworm control was determined five days later as follows: 0% control=no plant growth; 100% control=plant growth comparable to that in an uninfested cup.

| Compound | Percent Control |
|---|---|
| N,N'—[thiobis[(methylimino)-carbonyloxy]]bis[2,2,2-trifluoroethanimidothioic acid], dimethyl ester, Z,Z-isomer | 100 |
| N,N'—[thiobis[(methylimino)-carbonyloxy]]bis[2,2,2-trifluoroethanimidothioic acid], dimethyl ester, E,E-isomer | 100 |
| N,N'—[thiobis[(methylimino)-carbonyloxy]]bis[2,2,2-trifluoroethanimidothioic acid], dimethyl ester, E,Z-isomer | 100 |

EXAMPLE VII

A grain of corn was placed on Michigan peat in each of a series of cups (2 inches×2 inches). The cups were sprayed with 0.1% acetone solution of the indicated compounds. The grains were then covered with more peat, and each cup was infested with 10 larvae of the southern corn rootworm. Percent rootworm control was determined five days later as follows: 0% control=no plant growth; 100% control=plant growth comparable to that in an uninfested cup.

| Compound | Percent Control |
|---|---|
| N—[N—[N—(1-(methylthio)ethylideneaminooxycarbonyl)-N—methylaminothio]-N—methylaminocarbonyloxy]-2,2,2-trifluoroethanimidothioic acid, methyl ester | 100 |
| Dimethyl N,N'—[2,3-butanediylidenebis[nitrilooxycarbonyl-(N—methylimino)thio(N—methylimino)carbonyloxy]]bis[2,2,2-trifluoroethanimidothioate | 100 |

What is claimed is:
1. A compound of the formula:

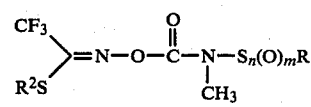

wherein

R is 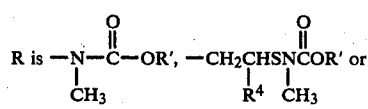

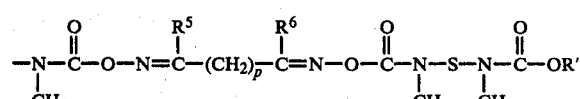

where
R' is

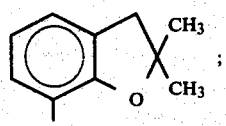

$R^2$ is $C_1$-$C_6$ alkyl; $C_3$-$C_6$ alkenyl, or

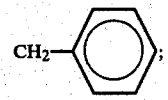

$R^4$ is H;
n is 1 or 2;
m is 0 or 1;
p is 0, 1 or 2;
$R^5$ or $R^6$ are independently H, $C_1$-$C_4$ alkyl, phenyl or phenyl substituted with one atom of F, Cl, Br or $CH_3$;
provided that when:
(1) R is

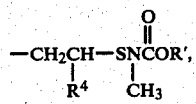

n must be 1;
(2) n is 2, m must be 0.

2. A compound of claim 1 wherein

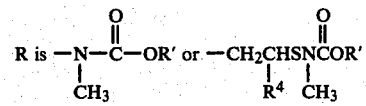

$R^2$ is $C_1$-$C_3$ alkyl;
$R^4$ is H.

3. A compound of claim 1 wherein
n is 1;
m is 0;
p is 0; and
$R^5$ and $R^6$ are independently H or $C_1$-$C_4$ alkyl.

4. An insecticide composition consisting essentially of a surfactant, diluent, and an effective amount of a compound of claim 1.

5. An insecticide composition consisting essentially of a surfactant, diluent, and an effective amount of a compound of claim 2.

6. An insecticide composition consisting essentially of a surfactant, diluent, and an effective amount of a compound of claim 3.

7. A method for controlling insects which comprises applying to a locus to be protected an insecticidally effective amount of a compound of claim 1.

8. A method for controlling insects which comprises applying to a locus to be protected an insecticidally effective amount of a compound of claim 2.

9. A method for controlling insects which comprises applying to a locus to be protected an insecticidally effective amount of a compound of claim 3.

* * * * *